United States Patent
Schulte et al.

(10) Patent No.: US 7,148,174 B2
(45) Date of Patent: Dec. 12, 2006

(54) NON-METALLOCENE CATALYST SYSTEM

(75) Inventors: Jörg L. Schulte, Frankfurt am Main (DE); Jörg Schottek, Frankfurt (DE)

(73) Assignee: Celanese Ventures GmbH, Frankfurt am Main (DE)

( * ) Notice: Subject to any disclaimer, the term of this patent is extended or adjusted under 35 U.S.C. 154(b) by 0 days.

(21) Appl. No.: 10/481,440

(22) PCT Filed: Jun. 19, 2002

(86) PCT No.: PCT/EP02/06772

§ 371 (c)(1),
(2), (4) Date: Sep. 23, 2004

(87) PCT Pub. No.: WO03/004506

PCT Pub. Date: Jan. 16, 2003

(65) Prior Publication Data

US 2005/0037918 A1   Feb. 17, 2005

(30) Foreign Application Priority Data

Jun. 22, 2001 (DE) ................. 101 30 229

(51) Int. Cl.
*B01J 31/22* (2006.01)
(52) U.S. Cl. ............ 502/103; 502/117; 502/150; 534/15; 556/9; 556/13
(58) Field of Classification Search ........ 502/103, 502/117, 150; 534/15; 556/9, 13
See application file for complete search history.

(56) References Cited

U.S. PATENT DOCUMENTS

| | | | |
|---|---|---|---|
| 4,465,630 A * | 8/1984 | Akashi et al. | 540/465 |
| 5,360,939 A * | 11/1994 | Stanley et al. | 568/454 |
| 5,744,620 A * | 4/1998 | Hsiao et al. | 549/533 |
| 5,981,424 A * | 11/1999 | Durante et al. | 502/165 |
| 6,124,231 A | 9/2000 | Fritze et al. | 502/152 |
| 6,211,107 B1 * | 4/2001 | Bell et al. | 502/150 |
| 6,255,531 B1 | 7/2001 | Fritz et al. | 568/3 |
| 6,271,164 B1 | 8/2001 | Fritze et al. | 502/104 |
| 6,350,829 B1 | 2/2002 | Lynch et al. | 526/151 |
| 6,391,406 B1 * | 5/2002 | Zenner et al. | 428/35.7 |
| 6,482,902 B1 | 11/2002 | Bohnen et al. | 526/127 |
| 6,781,006 B1 * | 8/2004 | Larrow et al. | 556/32 |
| 6,809,058 B1 * | 10/2004 | Boffa et al. | 502/167 |
| 6,864,334 B1 * | 3/2005 | Baugh et al. | 526/161 |
| 6,884,750 B1 * | 4/2005 | Kim et al. | 502/150 |
| 6,903,043 B1 * | 6/2005 | Kim et al. | 502/162 |
| 2006/0089252 A1 * | 4/2006 | Coates et al. | 502/150 |

FOREIGN PATENT DOCUMENTS

| | | |
|---|---|---|
| DE | 196 06 167 A1 | 8/1997 |
| DE | 196 22 207 A1 | 12/1997 |
| EP | 601 830 A2 | 6/1994 |
| EP | 601 830 A3 | 6/1994 |
| EP | 811 627 A2 | 12/1997 |
| EP | 811 627 A3 | 12/1997 |
| EP | 824 112 A1 | 2/1998 |
| EP | 824 113 A1 | 2/1998 |
| EP | 874 005 A1 | 10/1998 |
| EP | 924 223 A2 | 6/1999 |
| EP | 924 223 A3 | 6/1999 |
| WO | WO 94/28034 | 12/1994 |
| WO | WO 97/11775 A2 | 4/1997 |
| WO | WO 97/11775 A3 | 4/1997 |
| WO | WP 99/40129 | 8/1999 |

OTHER PUBLICATIONS

"Chiral Palladium(II) Complexes Bearing Tetradentate Nitrogen Ligands: Synthesis, Crystal Structure and Reactivity Towards the Polymerization of Norbornene", Abu-Surrah et al., Journal of Organometallic Chemistry 587, 1999, pp. 58-66.
"Stereoselective Formation of (Aminoalkyl)Platinum Complexes from Imines", Baar et al., Organometallics 20, 2001, pp. 408-417.
International Search Report in PCT/EP02/06772 dated Oct. 22, 2002.
International Preliminary Examination Report in PCT/EP02/06772 dated Feb. 3, 2003.

* cited by examiner

*Primary Examiner*—David M. Brunsman
(74) *Attorney, Agent, or Firm*—Marshall, Gerstein & Borun LLP

(57) ABSTRACT

The present invention describes a novel group of specific transition metal compounds, referred to as nonmetallocene compounds, and catalyst systems prepared therefrom. These catalyst systems which have become obtainable for the first time are suitable for the polymerization of olefins.

9 Claims, No Drawings

NON-METALLOCENE CATALYST SYSTEM

This application is a 371 of PCT/EP02/06772 Filed 19 Jun. 2002.

The present invention relates to a process for preparing specific transition metal compounds, to novel transition metal compounds and to their use for the polymerization of olefins.

In recent years, metallocenes have been used in addition to conventional Ziegler catalysts for olefin polymerization in order to generate polyolefins having particular properties which are not achieved using conventional Ziegler catalysts. Metallocenes can, if appropriate in combination with one or more cocatalysts, be used as catalyst components for the polymerization and copolymerization of olefins. In particular, halogen-containing metallocenes are used as catalyst precursors which can, for example, be converted into a polymerization-active cationic metallocene complex by means of an aluminoxane.

However, the preparation and use of metallocenes is at present still a cost factor which can be overcome neither by increased activity nor by improved synthetic methods. In addition, the conversion of such catalysts into a heterogeneous form presents a further problem since, in particular, the activities in this case are substantially decreased compared to the polymerization carried out in a homogeneous system.

The literature has described various "nonmetallocenes", for example in EP 874 005, which have advantages in terms of ease of preparation and the costs of the starting materials. The high activities of these complexes represent a further cost-saving factor. However, despite numerous compounds known from the literature, e.g. in J. Organomet. Chem. 1999, 587, 58–66, and Organometallics 2001, 20, 408–417, it has until now not been possible to develop "nonmetallocenes" which generate isotactic polypropylene having a satisfactory tacticity.

It is therefore an object of the invention to develop novel metal catalysts which open up a new advantageous route to polyolefins while avoiding the disadvantages of the prior art described.

Surprisingly, it has now been found that reaction of bridged ligands with transition metal compounds gives chiral transition metal complexes which are able to polymerize propene stereospecifically. This method of preparation represents a universal route to these novel classes of compounds. These compounds thus achieve the object of the invention.

The present invention provides compounds of the formula I

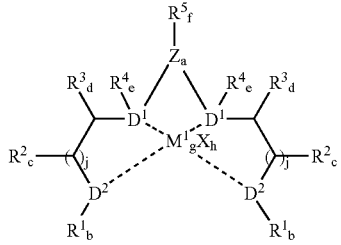

formula I where $M^1$ is a metal of groups III to XII of the Periodic Table of the Elements, in particular Sc, Y, La, Ti, Zr, Hf, V, Cr, Mo, Mn, Fe, Ru, Co, Rh, Ni, Pd or Cu and $D^1$ are identical or different and are each a donor atom of group XV or XVI of the Periodic Table of the Elements, in particular N, P, As, O, S, Se and Te and $D^2$ are identical or different and are each a donor atom of group XV or XVI of the Periodic Table of the Elements, in particular N, P, As, O, S, Se and Te and Z is a bridging structural element between the two donor atoms $D^1$ and X are identical or different and are each a hydrogen atom, a $C_1$–$C_{10}$-hydrocarbon group such as $C_1$–$C_{10}$-alkyl, $C_6$–$C_{10}$-aryl, $C_7$–$C_{20}$-alkylaryl, $C_7$–$C_{20}$-arylalkyl, $C_2$–$C_{20}$-alkenyl, $C_2$–$C_{20}$-alkynyl or a halogen atom or $OR^6$, $SR^6$, $OSO_2R^6$, $OSi(R^6)_3$, $Si(R^6)_3$, $P(R^6)_2$, $P(R^6)_3$, $NCR^6$, $N(R^6)_3$, $B(R^6)_4$, substituded or unsubstituted pyridine or $N(R^6)_2$, and $R^1$ are identical or different and are each a hydrogen atom, a $C_1$–$C_{20}$-alkyl group, a $C_6$–$C_{20}$-aryl group, a $C_7$–$C_{20}$-alkylaryl group, a $C_7$–$C_{30}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or a heteroatom-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or $Si(R^6)_3$, where one or more radicals $R^1$ together with one or more radicals $R^2$ may form a monocyclic or polycyclic ring system, e.g. pyridinyl, quinolinyl or isoquinolinyl, which may in turn be substituted by one or more radicals $R^6$, and $R^2$ are identical or different and are each a hydrogen atom, a $C_1$–$C_{20}$-alkyl group, a $C_6$–$C_{20}$-aryl group, a $C_7$–$C_{20}$-alkylaryl group, a $C_7$–$C_{30}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or a heteroatom-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or $Si(R^6)_3$, where one or more radicals $R^2$ together with one or more radicals $R^1$ and/or $R^3$ may form a monocyclic or polycyclic ring system, e.g. pyridinyl, quinolinyl or isoquinolinyl, which may in turn be substituted by one or more radicals $R^6$, and $R^3$ are identical or different and are each a hydrogen atom, a $C_1$–$C_{20}$-alkyl group, a $C_6$–$C_{20}$-aryl group, a $C_7$–$C_{20}$-alkylaryl group, a $C_7$–$C_{30}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or a heteroatom-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or $Si(R^6)_3$, where one or more radicals $R^3$ together with one or more radicals $R^2$ may form a monocyclic or polycyclic ring system, e.g. pyridinyl, quinolinyl or isoquinolinyl, which may in turn be substituted by one or more radicals $R^6$, and $R^4$ are identical or different and are each a hydrogen atom, a $C_1$–$C_{20}$-alkyl group, a $C_6$–$C_{20}$-aryl group, a $C_7$–$C_{20}$-alkylaryl group, a $C_7$–$C_{30}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or a heteroatom-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group or C$_2$–C$_{20}$-alkynyl group, and R$^5$ are identical or different and are each a hydrogen atom, a C$_1$–C$_{20}$-alkyl group, a C$_6$–C$_{20}$-aryl group, a C$_7$–C$_{20}$-alkylaryl group, a C$_7$–C$_{30}$-arylalkyl group, a C$_2$–C$_{20}$-alkenyl group, a C$_2$–C$_{20}$-alkynyl group or a halogen-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or a heteroatom-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group, where a plurality of radicals R$^5$ may together form a monocyclic or polycyclic ring system, and R$^6$ are identical or different and are each a hydrogen atom, a halogen atom, a C$_1$–C$_{10}$-alkyl group, a C$_6$–C$_{20}$-aryl group, a C$_7$–C$_{20}$-alkylaryl group, a C$_7$–C$_{30}$-arylalkyl group, a C$_2$–C$_{20}$-alkenyl group, a C$_2$–C$_{20}$-alkynyl group or a halogen-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or a heteroatom-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group, and a are identical or different and are each an integer from 1 to 10 and b are identical or different and are each an integer from 0 to 3 and c are identical or different and are each an integer from 0 to 2 and d are identical or different and are each an integer from 0 to 2 and e are identical or different and are each an integer from 0 to 2 and f are identical or different and are each an integer from 2 to 20 and g are identical or different and are each 1 or 2 and h are identical or different and are each an integer from 1 to 4 and i are identical or different and are each an integer from 0 to 24 and j are identical or different and are each an integer from 0 to 10, with the proviso that complexes in which Z$_a$(R$^5$)$_f$ is unsubstituted or substituted ethyl and D$^1$ is nitrogen, R$^3$ is hydrogen, d is 1 and two R$^2$ together form a substituted benzene ring which is substituted by D$^2$=O, i.e. salen complexes, are excepted from the scope of the invention.

Illustrative but nonlimiting examples of D$^1$—Z$^1$(R$^5$)$_f$—D$^1$ are:

formula II a-z

II a

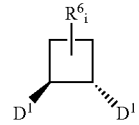
II b

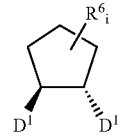
II c

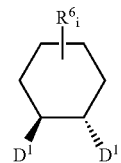
II d

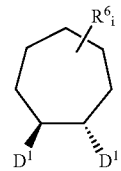
II e

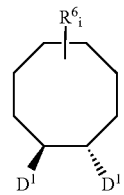
II f

II g

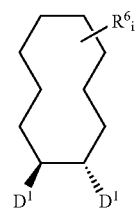
II h

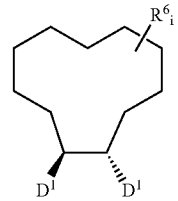
II i

-continued

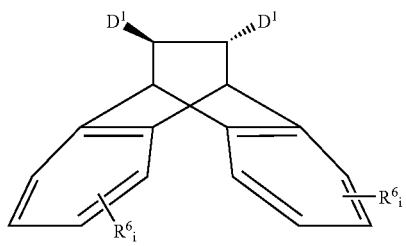

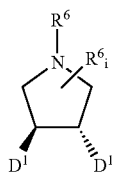

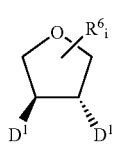

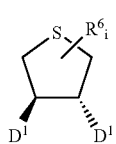

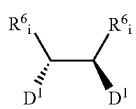

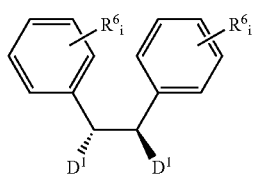

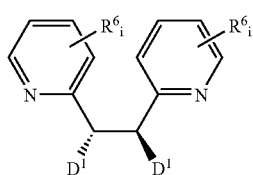

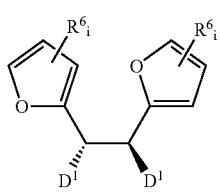

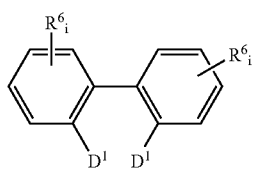

-continued

II j

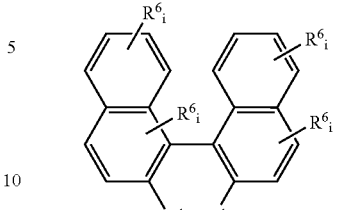

II k

II l

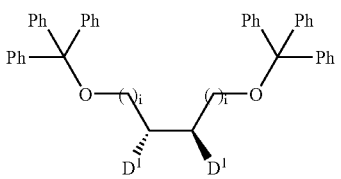

II m

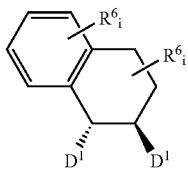

II n

II o

II p

II q

II r

II s

II t

II u

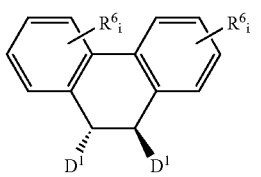

II v

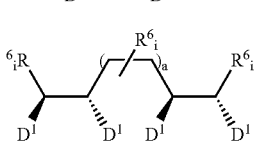

II w

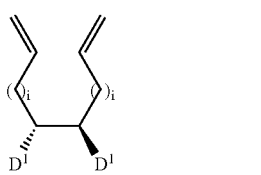

II x

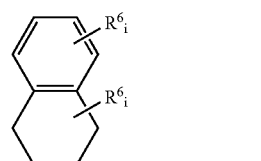

II y

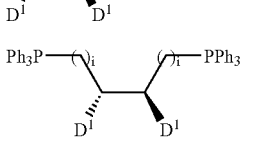

II z

Preference is given to transition metal compounds of the formula I in which $M^1$ is a metal of groups III to XII of the Periodic Table of the Elements, in particular Sc, Y, Ti, Zr, Hf, Cr, Mn, Fe, Ru, Co, Rh, Ni, Pd or Cu and $D^1$ are identical or different and are each a donor atom of group XV or XVI of the Periodic Table of the Elements, in particular N, P, O or S, and $D^2$ are identical or different and are each a donor atom of group XV or XVI of the Periodic Table of the Elements, in particular N, P, O or S, and Z is a bridging structural element between the two donor atoms $D^1$, in particular a structural element of the formula II a-z, and X are identical or different and are each a $C_1$–$C_{10}$-hydrocarbon group such as $C_1$–$C_5$-alkyl, $C_6$–$C_{10}$-aryl, $C_7$–$C_{11}$-alkylaryl, $C_7$–$C_{11}$-arylalkyl, $C_2$–$C_{10}$-alkenyl, $C_2$–$C_{10}$-alkynyl or a halogen atom or $OR^6$, $SR^6$, $OSO_2R^6$, $OSi(R^6)_3$, $Si(R^6)_3$, $P(R^6)_2$, $P(R^6)_3$, $NCR^6$, $N(R^6)_3$, $B(R^6)_4$, substituted or unsubstituted pyridine or $N(R^6)_2$, and $R^1$ are identical or different and are each a hydrogen atom, a $C_1$–$C_{10}$-alkyl group, a $C_6$–$C_{10}$-aryl group, a $C_7$–$C_{11}$-alkylaryl group, a $C_7$–$C_{11}$-arylalkyl group, a $C_2$–$C_{10}$-alkenyl group, a $C_2$–$C_{10}$-alkynyl group or a halogen-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group, $C_2$–$C_{10}$-alkynyl group or a heteroatom-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group, $C_2$–$C_{10}$-alkynyl group or $Si(R^6)_3$, where one or more, radicals $R^1$ together with one or more radicals $R^2$ may form a monocyclic or polycyclic ring system, e.g. pyridinyl, quinolinyl or isoquinolinyl, which may in turn be substituted by one or more radicals $R^6$, and $R^2$ are identical or different and are each a hydrogen atom, a $C_1$–$C_{10}$-alkyl group, a $C_6$–$C_{10}$-aryl group, a $C_7$–$C_{11}$-alkylaryl group, a $C_7$–$C_{11}$-arylalkyl group, a $C_2$–$C_{10}$-alkenyl group, a $C_2$–$C_{10}$-alkynyl group or a halogen-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group, $C_2$–$C_{10}$-alkynyl group or a heteroatom-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group, $C_2$–$C_{10}$-alkynyl group or $Si(R^6)_3$, where one or more radicals $R^2$ together with one or more radicals $R^1$ and/or $R^3$ may form a monocyclic or polycyclic ring system, e.g. pyridinyl, quinolinyl or isoquinolinyl, which may in turn be substituted by one or more radicals $R^6$, and $R^3$ are identical or different and are each a hydrogen atom, a $C_1$–$C_{10}$-alkyl group, a $C_6$–$C_{10}$-aryl group, a $C_7$–$C_{11}$-alkylaryl group, a $C_7$–$C_{11}$-arylalkyl group, a $C_2$–$C_{10}$-alkenyl group, a $C_2$–$C_{10}$-alkynyl group or a halogen-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group, $C_2$–$C_{10}$-alkynyl group or a heteroatom-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group, $C_2$–$C_{10}$-alkynyl group or $Si(R^6)_3$, where one or more radicals $R^3$ together With one or more radicals $R^2$ may form a monocyclic or polycyclic ring system, e.g. pyridinyl, quinolinyl or isoquinolinyl, which may in turn be substituted by one or more radicals $R^6$, and $R^4$ are identical or different and are each a hydrogen atom, a $C_1$–$C_{10}$-alkyl group, a $C_6$–$C_{10}$-aryl group, a $C_7$–$C_{11}$-alkylaryl group, a $C_7$–$C_{11}$-arylalkyl group, a $C_2$–$C_{10}$-alkenyl group, a $C_2$–$C_{10}$-alkynyl group or a halogen-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group, $C_2$–$C_{10}$-alkynyl group or a heteroatom-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group or $C_2$–$C_{10}$-alkynyl group, and $R^5$ are identical or different and are each a hydrogen atom, a $C_1$–$C_{11}$-alkyl group, a $C_6$–$C_{10}$-aryl group, a $C_7$–$C_{11}$-alkylaryl group, a $C_7$–$C_{11}$-arylalkyl group, a $C_2$–$C_{10}$-alkenyl group, a $C_2$–$C_{10}$-alkynyl group or a halogen-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group, $C_2$–$C_{10}$-alkynyl group or a heteroatom-containing $C_1$–$C_{10}$-alkyl group, $C_6$–$C_{10}$-aryl group, $C_7$–$C_{11}$-alkylaryl group, $C_7$–$C_{11}$-arylalkyl group, $C_2$–$C_{10}$-alkenyl group, $C_2$–$C_{10}$-alkynyl group, where a plurality of radicals $R^5$ may together form a monocyclic or polycyclic ring system, and $R^6$ are identical or different and are each a hydrogen atom, a halogen atom, a $C_1$–$C_{10}$ alkyl group, a $C_6$–$C_{20}$-aryl group, a $C_7$–$C_{20}$-alkylaryl group, a $C_7$–$C_{30}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or a heteroatom-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group, and a are identical or different and are each an integer from 1 to 4 and b are identical or different and are each an integer from 0 to 2 and c are identical or different and are each an integer from 0 to 2 and d are identical or different and are each an integer from 0 to 2 and e are identical or different and are each an integer from 0 to 2 and f are identical or different and are each an integer from 2 to 20 and g are identical or different and are each 1 or 2 and h are identical or different and are each an integer from 1 to 4 and i are identical or different and are each an integer from 0 to 24 and j are identical or different and are each an integer from 0 to 10, with the proviso that complexes in which $Z_a(R^5)_f$ is unsubstituted or substituted ethyl and $D^1$ is nitrogen, $R^3$ is hydrogen, d is 1 and two $R^2$ together form a substituted benzene ring which is substituted by $D^2$=O, i.e. salen complexes, are excepted from the scope of the invention.

Very particular preference is given to compounds of the formula I in which $M^1$ is a metal of groups III to XII of the Periodic Table of the Elements, in particular Ti, Zr, Hf, Fe, Co, Ni or Pd and $D^1$ are identical or different and are each donor atom of group XV or XVI of the Periodic Table of the Elements, in particular N, P, O or S, and $D^2$ are identical or different and are each a donor atom of group XV or XVI of the Periodic Table of the Elements, in particular N, P, O or S, and Z corresponds to one of the formulae II d, II j, II o, II r and II s and X are identical or different and are each chloride, bromide, iodide, methyl, ethyl, propyl, ethenyl, propynyl, phenyl, benzyl, methoxy, trifluoromethanesulfonyl, dimethylamido, tetrafluoroborate, triphenylphosphine, acetonitrile, trimethylsilyl or pyridine, and $R^1$ are identical or different and are each a hydrogen atom, methyl, ethyl, propyl, i-propyl, tert-butyl, phenyl, benzyl, trimethylsilyl or tert-butyldimethylsilyl, or a radical $R^1$ together with a radical $R^2$ forms a monocyclic or polycyclic ring system, preferably pyridinyl, quinolinyl or isoquinolinyl, which may in turn be substituted by one or more radicals $R^6$, and $R^2$ are identical or different and are each a hydrogen atom, methyl, ethyl, propyl, i-propyl, tert-butyl, phenyl, benzyl, trimethylsilyl or tert-butyldimethylsilyl, or a radical $R^2$ together with a radical $R^1$ forms a monocyclic or polycyclic ring system, preferably pyridinyl, quinolinyl or isoquinolinyl, which may in turn be substituted by one or more radicals $R^6$, and $R^3$ are identical or different and are each a hydrogen atom, methyl, ethyl, propyl, i-propyl, tert-butyl, phenyl, benzyl, trimethylsilyl or tert-butyldimethylsilyl, and $R^4$ are identical or different and are each a hydrogen atom, methyl, ethyl, propyl, i-propyl, tert-butyl, phenyl, benzyl, trimethylsilyl or tert-butyldimethylsilyl, and $R^5$ are identical or different and are each a hydrogen atom, methyl, ethyl, propyl, i-propyl, tert-butyl, phenyl, benzyl, trimethylsilyl or tert-butyldimethylsilyl, or a plurality of radicals $R^5$ may together form a monocyclic or polycyclic ring system, and $R^6$ are identical or different and are each a hydrogen atom, fluorine, chlorine, bromine, iodine, methyl, ethyl, propyl, i-propyl, tert-butyl, phenyl, benzyl, trimethylsilyl or tert-butyldimethylsilyl, and a are identical or different and are each 1 or 2 and b are identical or different and are each an integer from 0 to 2 and c are identical or different and are each an integer from 0 to 2 and d are identical or different and are each an integer from 0 to 2 and e are identical or different and are each 0 or 1 and f are identical or different and are each an integer from 2 to 20 and g are identical or different and are each 1 or 2 and h are identical or different and are each an integer from 1 to 4 and i are identical or different and are each an integer from 0 to 18 and j are identical or different and are each an integer from 0 to 6, with the proviso that complexes in which $Z_a(R^5)_f$ is unsubstituted or substituted ethyl and $D^1$ is nitrogen, $R^3$ is hydrogen, d is 1 and two $R^2$ together form a substituted benzene ring which is substituted by $D^2=O$, i.e. salen complexes, are excepted from the scope of the invention.

Illustrative but nonlimiting examples of compounds of the formula I are:

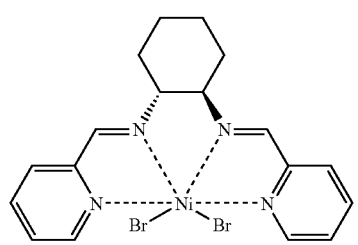

-continued

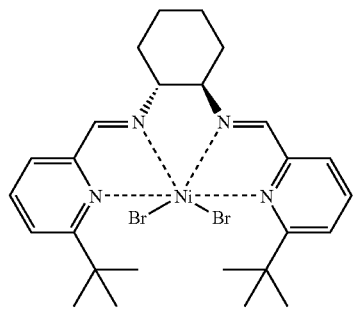

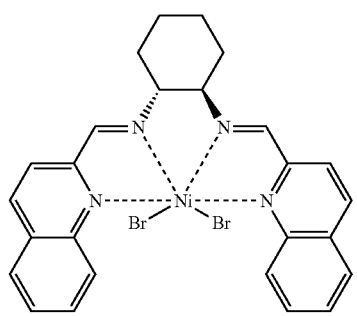

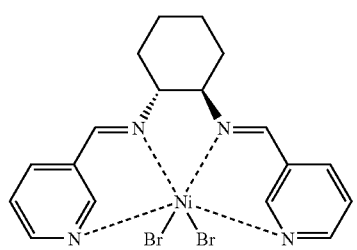

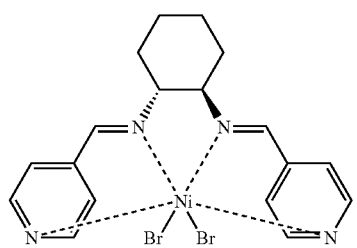

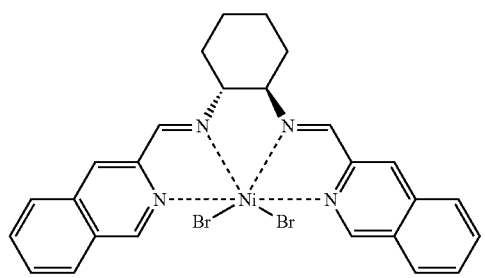

-continued
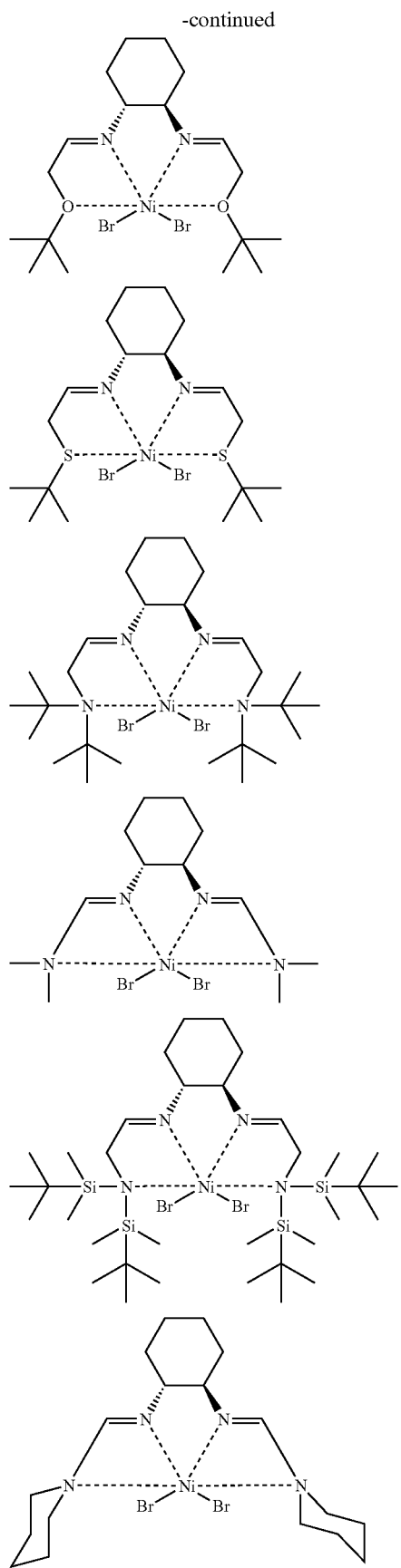
-continued
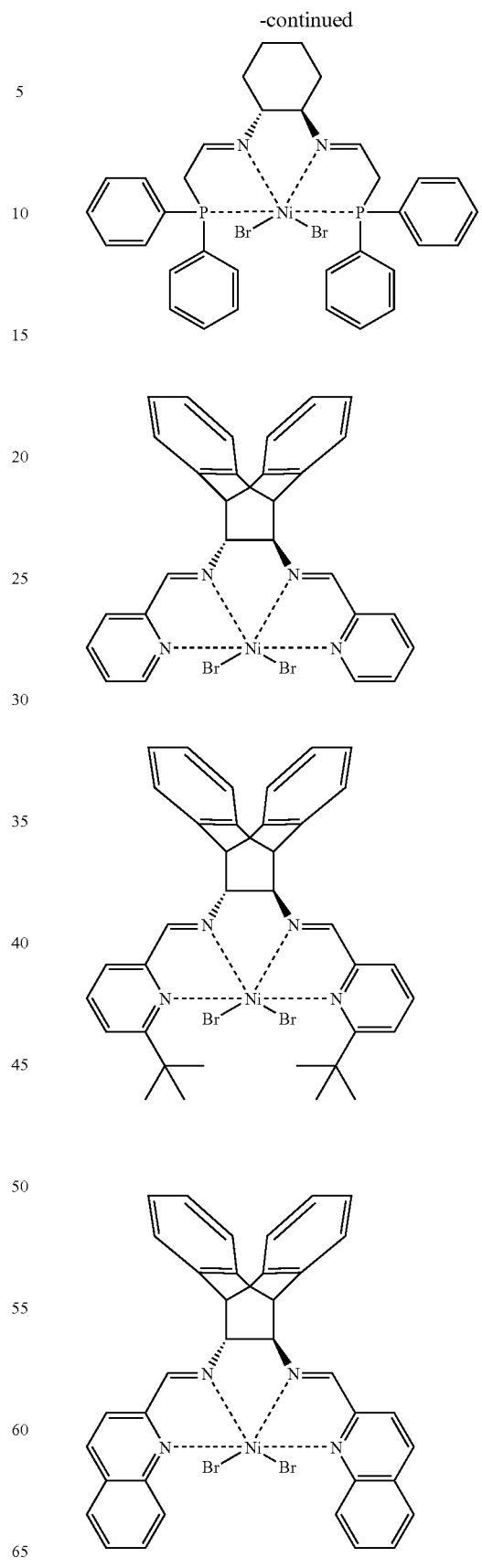

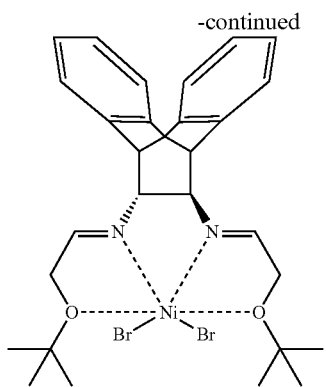
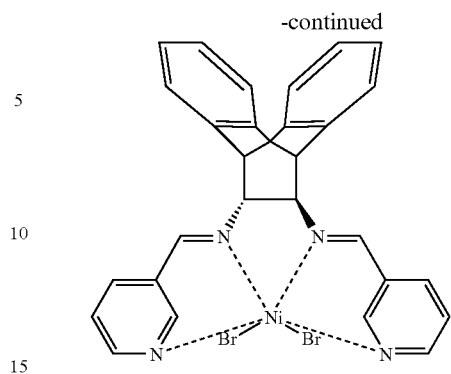
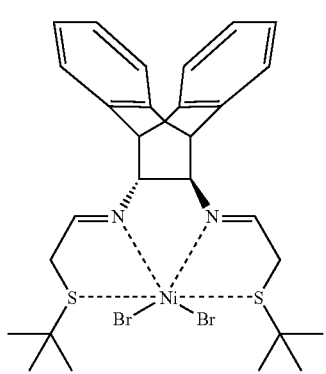
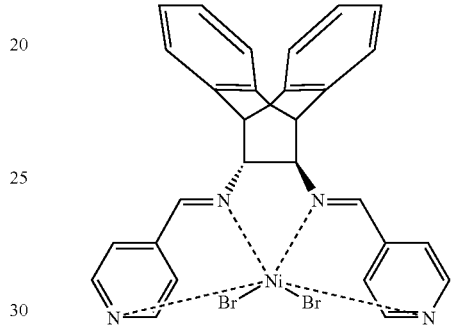
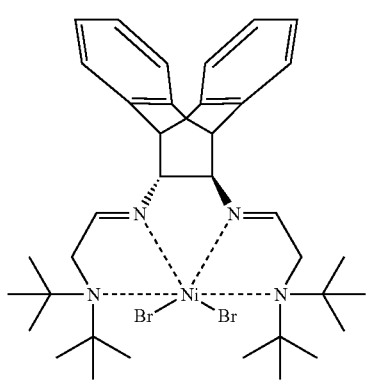
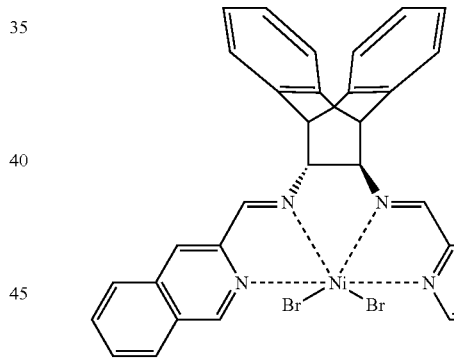
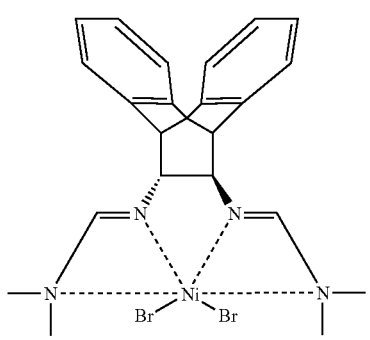
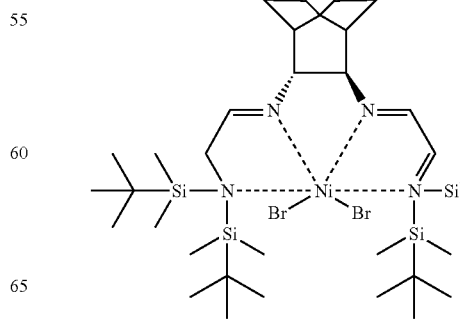

-continued
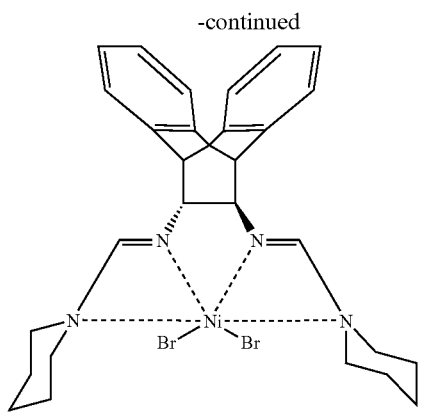
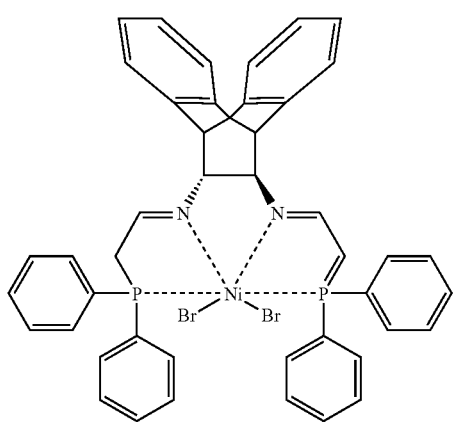
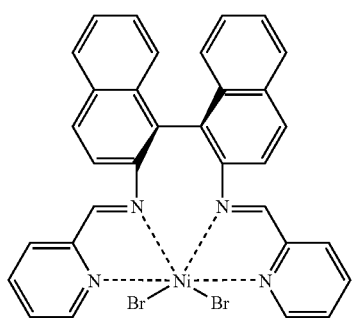
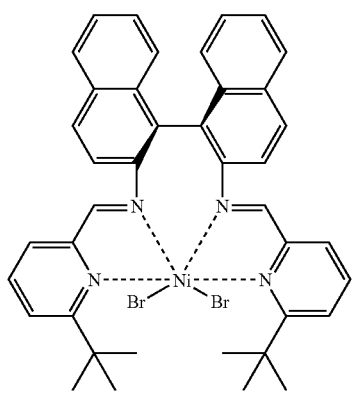
-continued
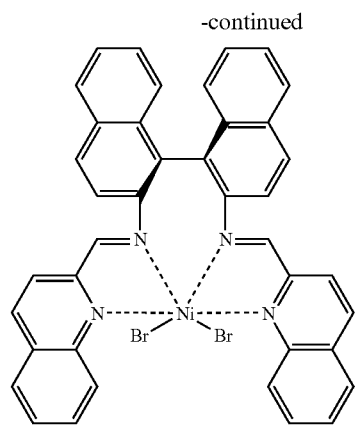
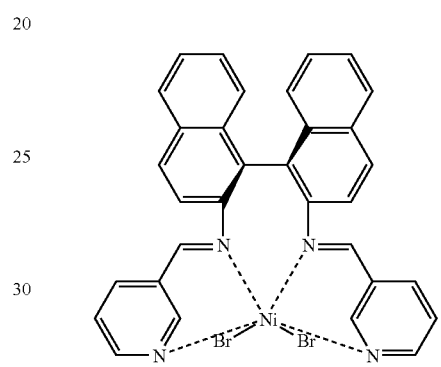
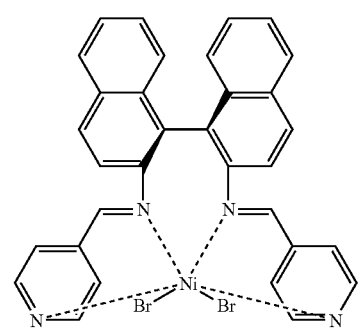
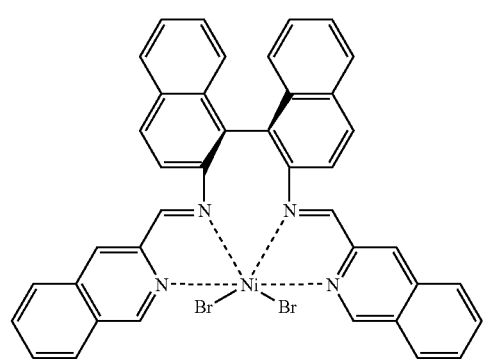

-continued
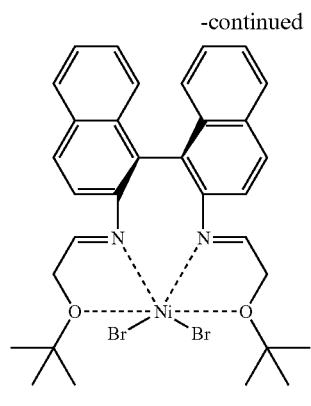
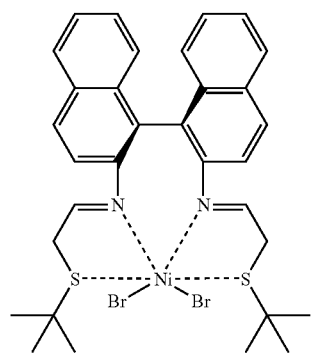
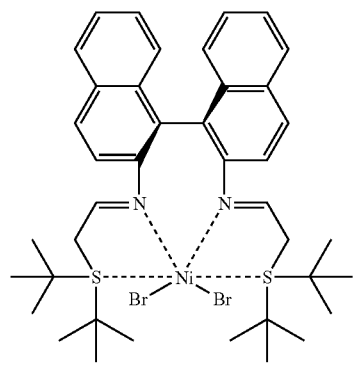
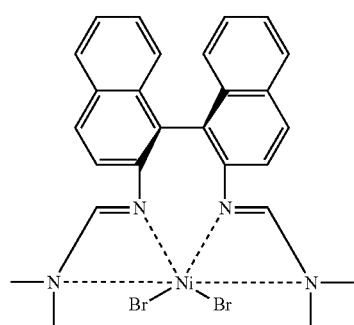
-continued
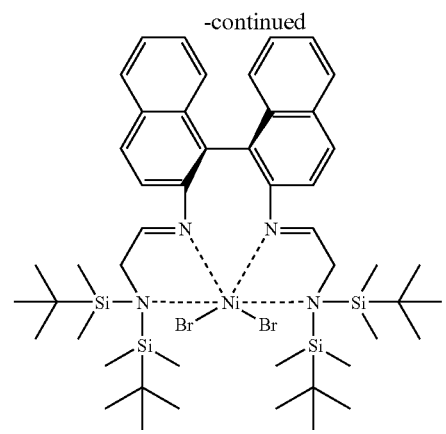
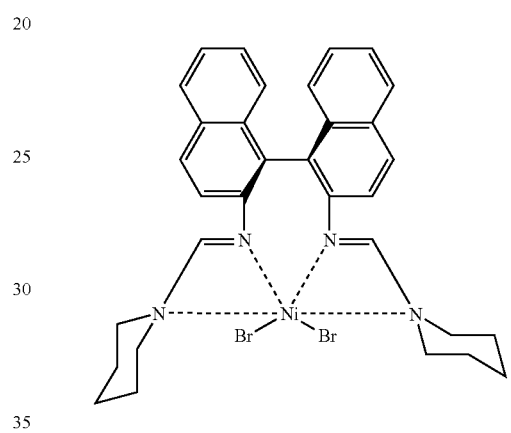
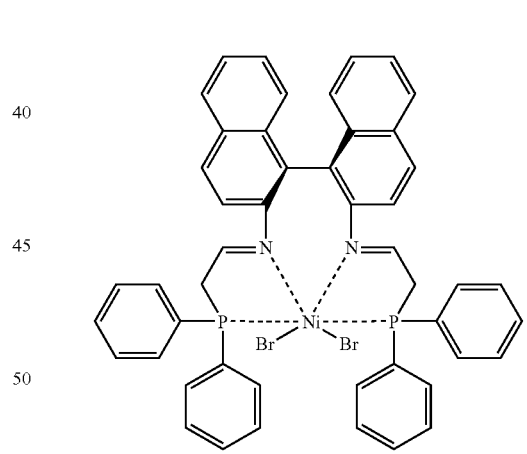
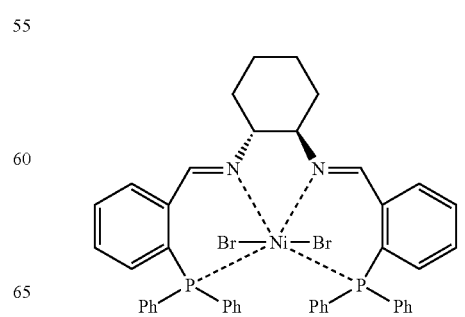

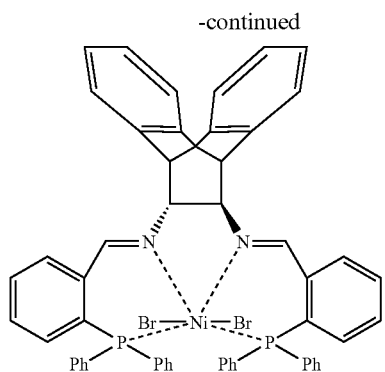
and the corresponding iron, cobalt, nickel and palladium complexes and the corresponding complexes in which X has the abovementioned meanings.
Further illustrative but nonlimiting examples of compounds of the formula I are:
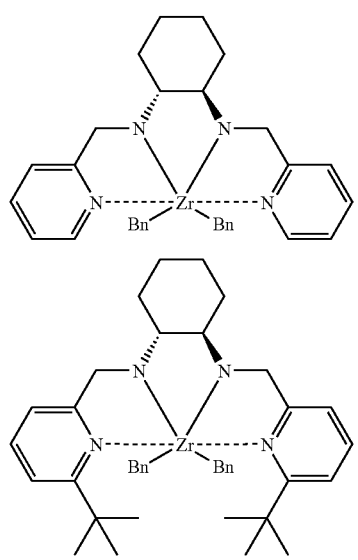
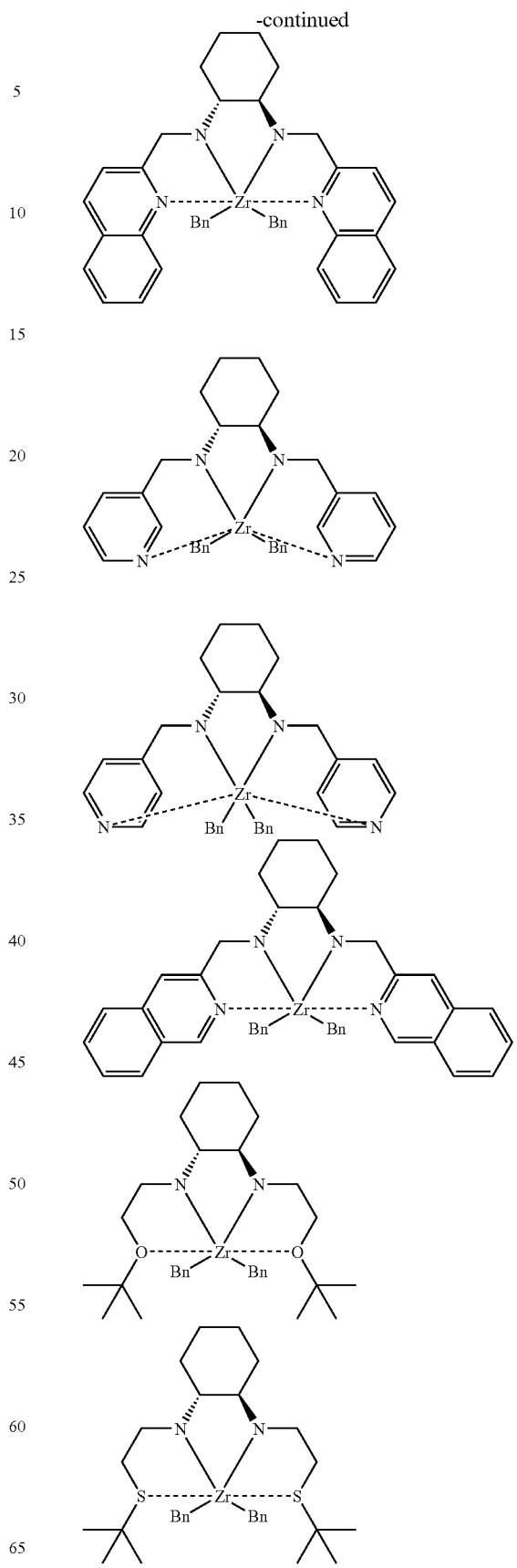

-continued
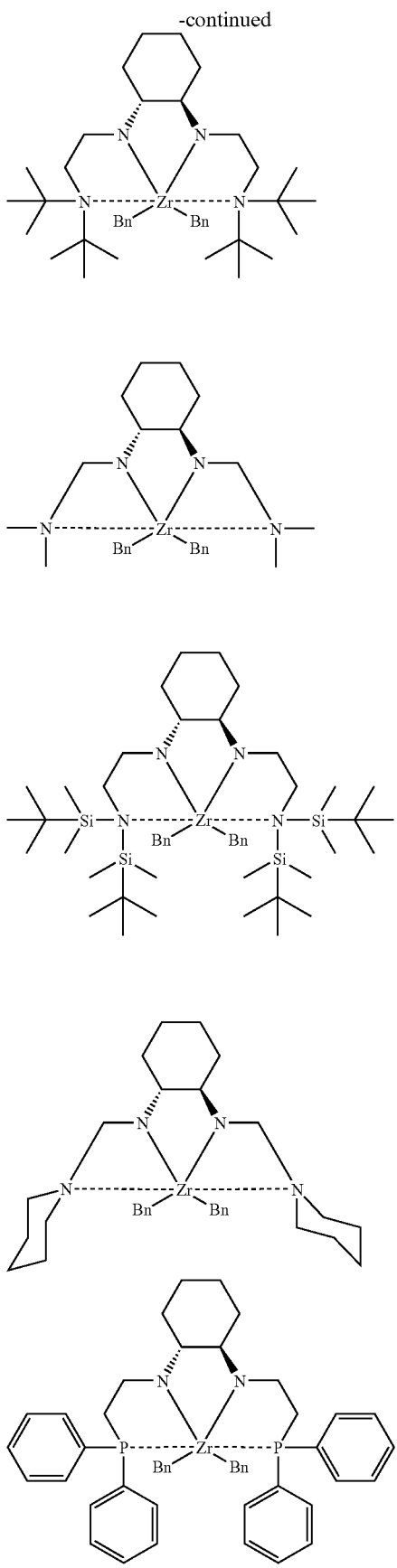
-continued
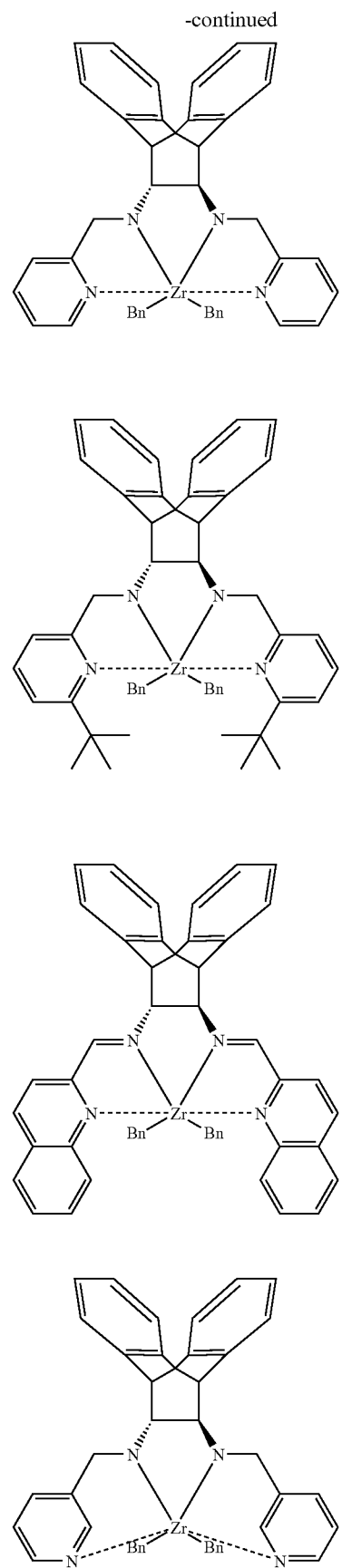

-continued
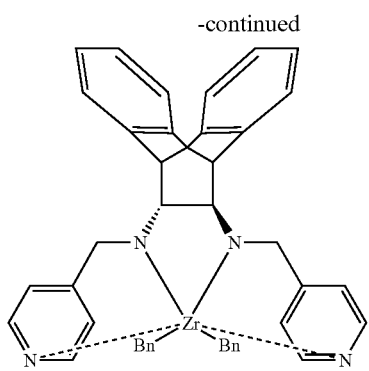
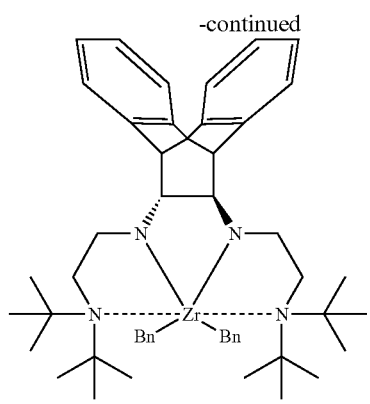
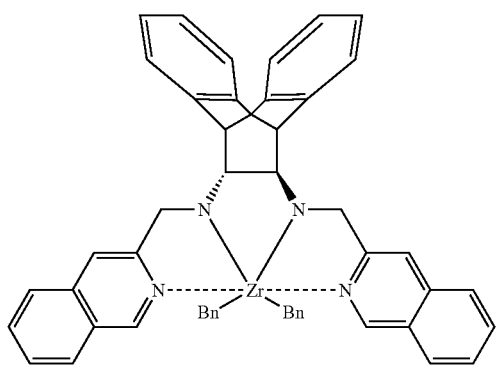
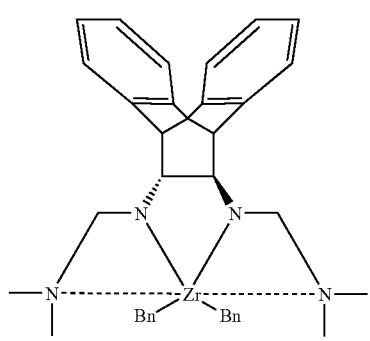
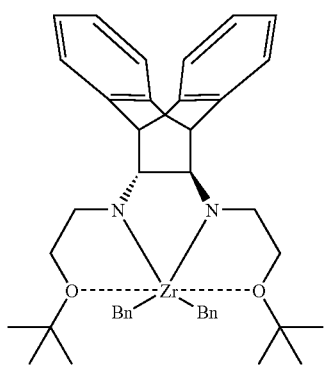
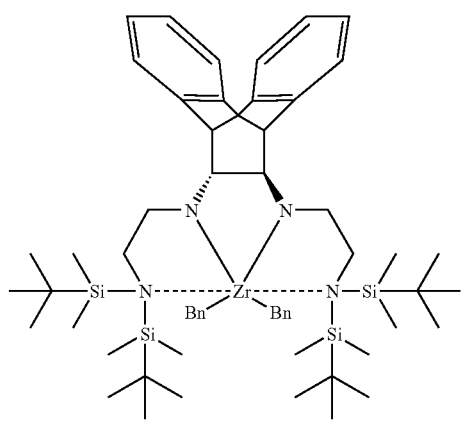
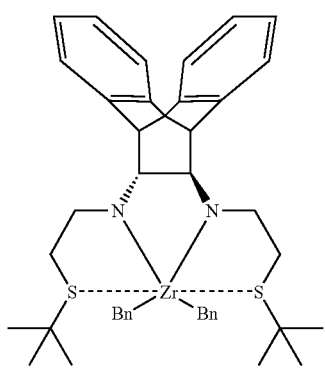
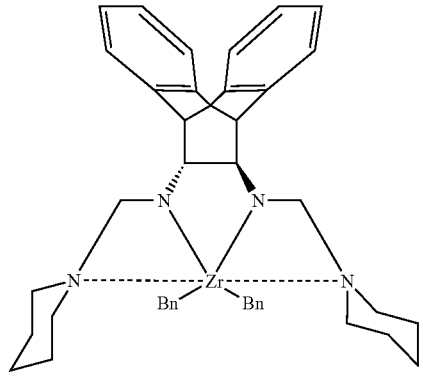

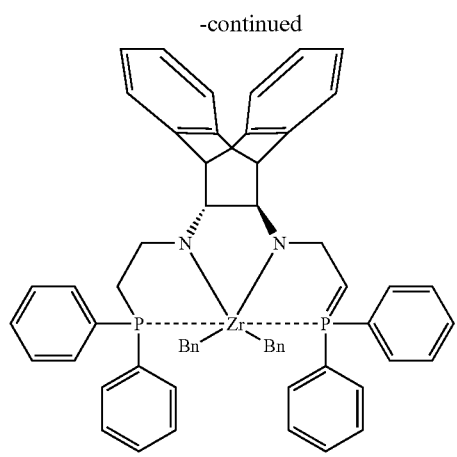
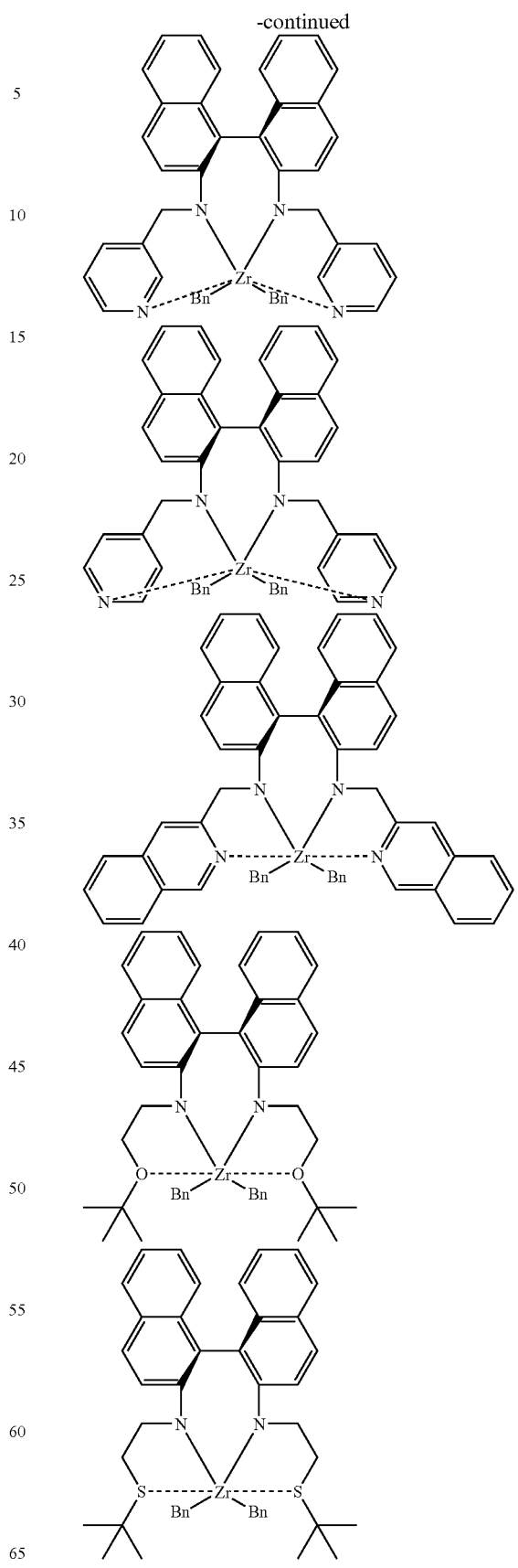

-continued
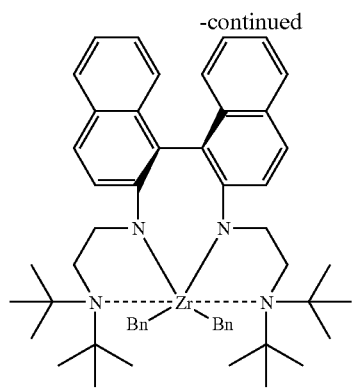
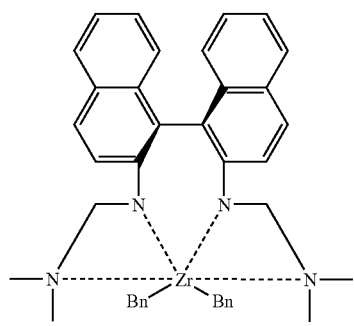
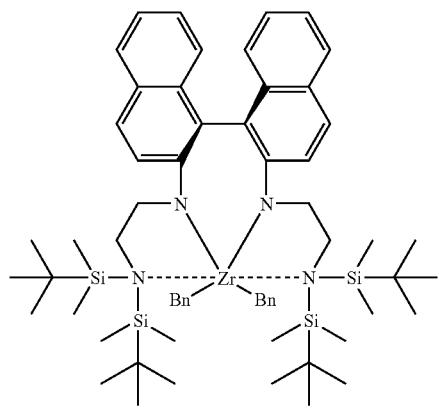
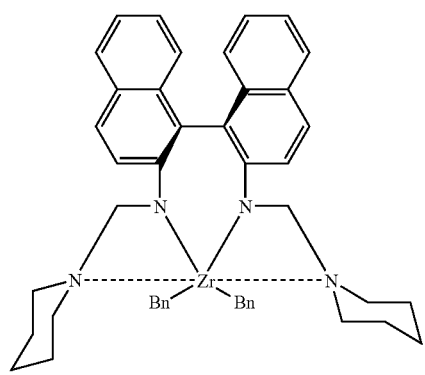
-continued
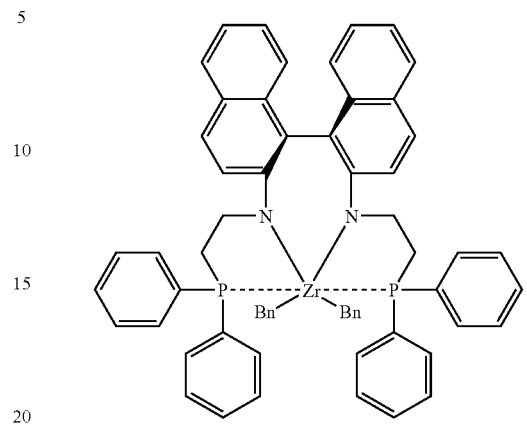
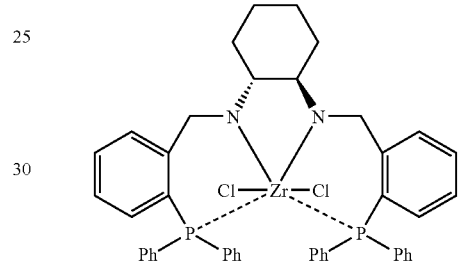
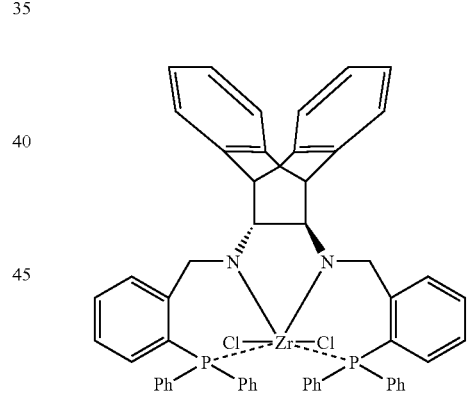
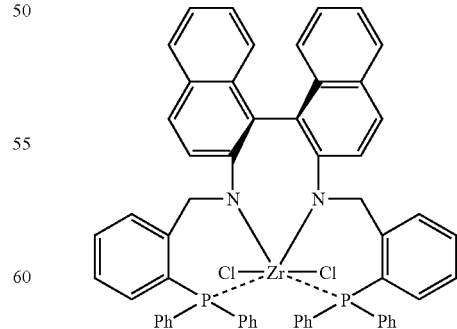
in which Bn is benzyl, and also the corresponding titanium and hafnium complexes and the corresponding complexes in which X has the abovementioned meanings.

SYNTHESIS EXAMPLES

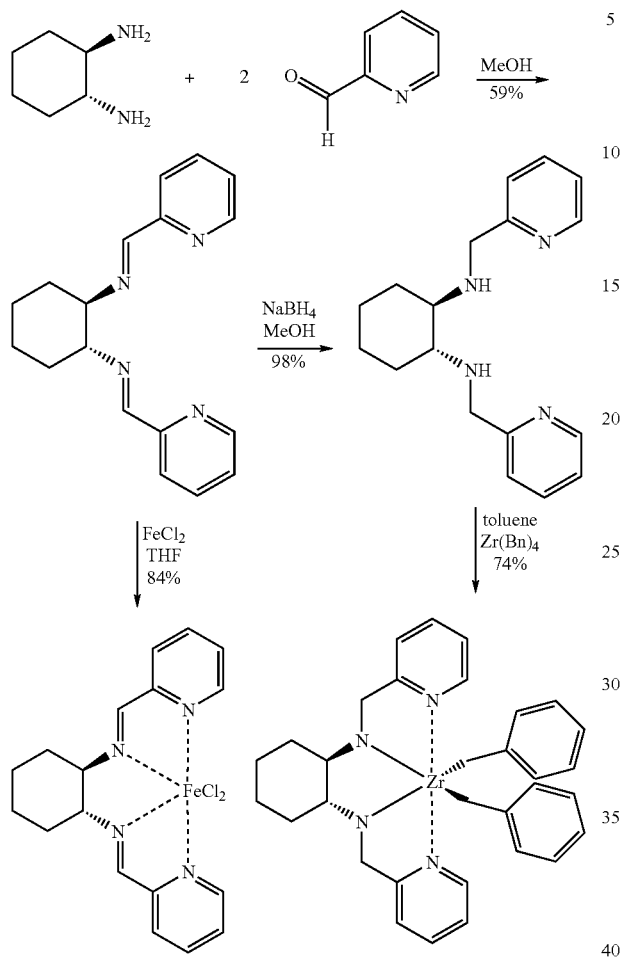

The ligands having a bisimine structure can be obtained by condensation of bisamines with aldehydes or ketones. The bisamine ligands are prepared by reduction of the corresponding bisimines or by alkylation of bisamines with customary alkylating reagents, e.g. arylalkyl halides, with addition of bases in a solvent. The reaction of bisimines with transition metal salts such as iron(II) chloride, nickel(II) bromide*DME, cobalt(II) chloride or bisacetonitrilepalladium dichloride in a solvent such as tetrahydrofuran or dichloromethane gives the corresponding transition metal complexes. The reaction of ligands having a bisamine structure with transition metal compounds such as tetrabenzylzirconium, tetrakis(dimethylamido)zirconium, tetrabenzyltitanium, tetrakis(dimethylamido)titanium, tetrabenzylhafnium or tetrakis(dimethylamido)hafnium in a solvent such as benzene, toluene or tetrahydrofuran gives the corresponding transition metal complexes. Furthermore, complexes of this structural type can also be obtained by deprotonation of the bisamine ligand with a base in a solvent such as toluene or THF or a solvent mixture, followed by reaction with transition metal halides such as zirconium tetrachloride, titanium tetrachloride or hafnium tetrachloride.

Salens, i.e. complexes in which $Z_a(R^5)_f$ unsubstituted or substituted ethyl and $D^1$ is nitrogen, $R^3$ is hydrogen, d is 1 and two $R^2$ together form a substituted benzene ring which is substituted by $D^2$=oxygen, and the following complexes are excluded from the invention:

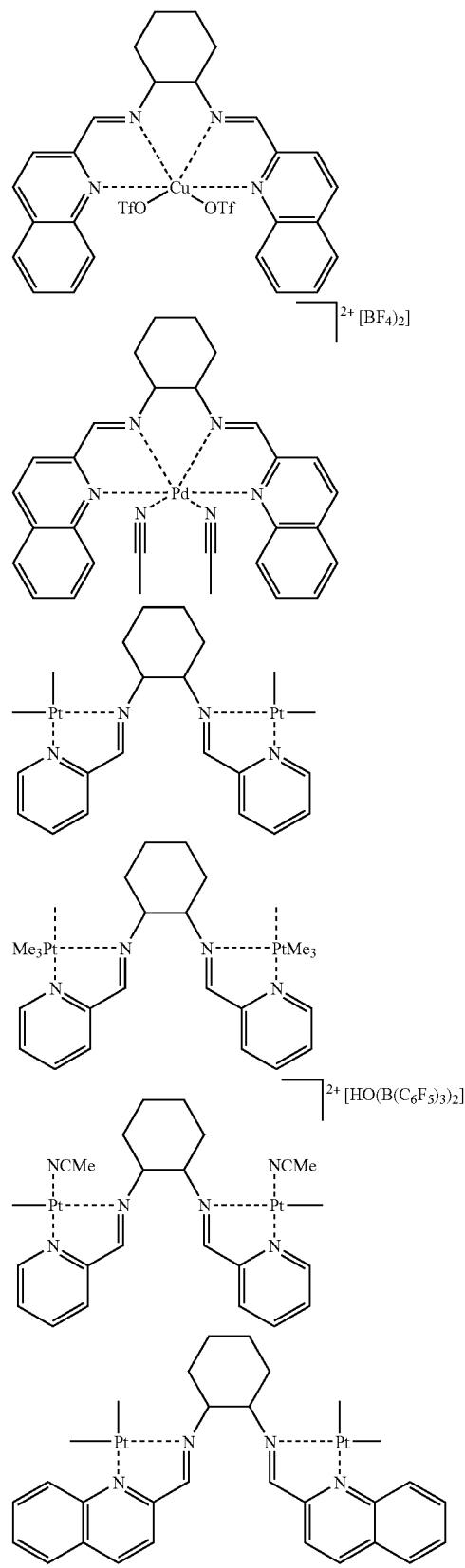

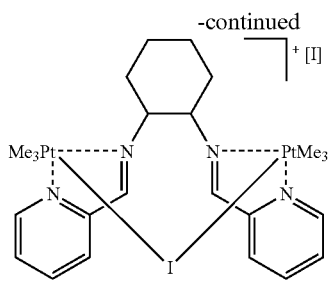

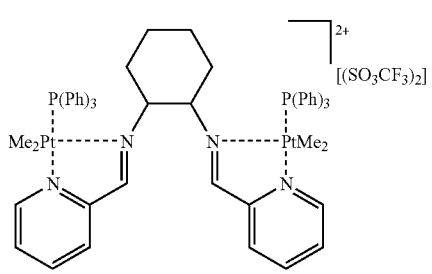

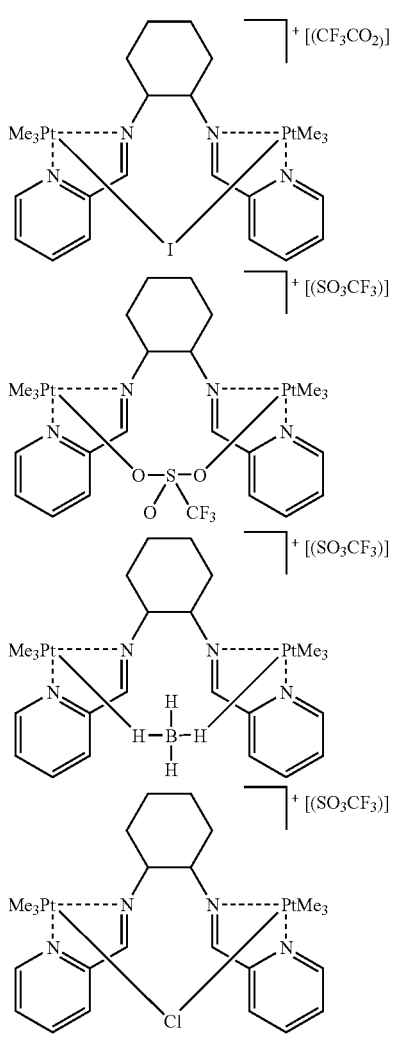

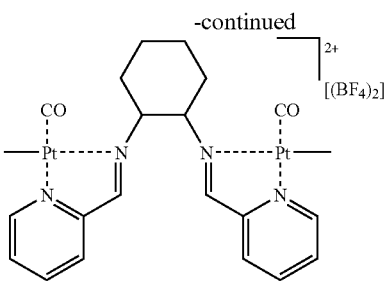

The present invention further provides a catalyst system comprising the novel chemical compound of the formula I.

The novel metal complexes of the formula I are particularly suitable as constituents of catalyst systems for preparing polyolefins by polymerization of at least one olefin in the presence of a catalyst comprising at least one cocatalyst and at least one metal complex of the formula I.

The cocatalyst which together with a novel transition metal complex of the formula I forms the catalyst system comprises at least one compound such as an aluminoxane or a Lewis acid or an ionic compound which reacts with a metal complex to convert it into a cationic compound.

As aluminoxane, preference is given to using a compound of the formula (III)

$$(R\ AlO)_n \quad (III).$$

Further suitable aluminoxanes can be, for example, cyclic as in the formula (IV)

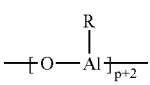

(IV)

or linear as in the formula (V)

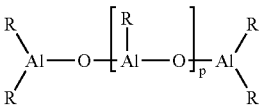

(V)

or of the cluster type as in the formula (VI)

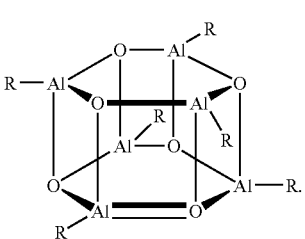

(VI)

Such aluminoxanes are described, for example, in JACS 117 (1995), 6465–74, Organometallics 13 (1994), 2957–2969.

The radicals R in the formulae (III), (IV), (V) and (VI) can be identical or different and can each be a $C_1$–$C_{20}$-hydrocarbon group such as a $C_1$–$C_6$-alkyl group, a $C_6$–$C_{18}$-aryl group, benzyl or hydrogen and p can be an integer from 2 to 50, preferably from 10 to 35.

Preference is given to the radicals R being identical and each being methyl, isobutyl, n-butyl, phenyl or benzyl, particularly preferably methyl.

If the radicals R are different, they are preferably methyl and hydrogen, methyl and isobutyl or methyl and n-butyl, with hydrogen or isobutyl or n-butyl preferably being present in an amount of 0.01 –40% (of the number of radicals R).

The aluminoxane can be prepared in various ways by known methods. One of the methods is, for example, reacting an aluminum-hydrocarbon compound and/or a hydridoaluminum-hydrocarbon compound with water (gaseous, solid, liquid or bound, for example as water of crystallization) in an inert solvent (e.g. toluene).

To prepare an aluminoxane having different alkyl groups R, two different trialkylaluminums ($AlR_3$+$AlR'_3$) corresponding to the desired composition and reactivity are reacted with water (cf. S. Pasynkiewicz, Polyhedron 9 (1990) 429 and EP-A-0,302,424).

Regardless of the method of preparation, all aluminoxane solutions have a varying content of unreacted aluminum starting compound which is present in free form or as adduct.

As Lewis acid, preference is given to using at least one organoboron or organoaluminum compound containing $C_1$–$C_{20}$ groups such as branched or unbranched alkyl or haloalkyl, e.g. methyl, propyl, isopropyl, isobutyl, trifluoromethyl, unsaturated groups such as aryl or haloaryl, e.g. phenyl, tolyl, benzyl groups, p-fluorophenyl, 3,5-difluorophenyl, pentachlorophenyl, pentafluorophenyl, 3,4,5 trifluorophenyl and 3,5 di(trifluoromethyl)phenyl.

Examples of Lewis acids are trimethylaluminum, triethylaluminum, triisobutylaluminum, tributylaluminum, trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane and/or tris(3,4,5-trifluorophenyl)borane. Particular preference is given to tris(pentafluorophenyl)borane.

As ionic cocatalysts, preference is given to using compounds which contain a noncoordinating anion, for example tetrakis(pentafluorophenyl)borate, tetraphenylborate, $SbF_6$—, $CF_3SO_3$— or $ClO_4$—. As cationic counterions, use is made of protonated Lewis bases such as methylamine, aniline, N,N-dimethylbenzylamine and derivatives thereof, N,N-dimethylcyclohexylamine and derivatives thereof, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene or triphenylcarbenium.

Examples of such ionic compounds are
triethylammonium tetra(phenyl)borate,
tributylammonium tetra(phenyl)borate,
trimethylammonium tetra(tolyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)boratee,
tributylammonium tetra(trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl)aluminate,
N,N-dimethylcyclohexylammonium tetrakis(pentafluorophenyl)borate,
N,N-dimethylbenzylammonium tetrakis(pentafluorophenyl)borate,
di(propyl)ammonium tetrakis(pentafluorophenyl)borate,
di(cyclohexyl)ammonium tetrakis(pentafluorophenyl)borate,
triphenylphosphonium tetrakis(phenyl)borate,
triethylphosphonium tetrakis(phenyl)borate,
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Preference is given to triphenylcarbenium tetrakis(pentafluorophenyl)borate and/or N,N-dimethylanilinium tetrakis(pentafluorophenyl)borate.

It is also possible to use mixtures of at least one Lewis acid and at least one ionic compound.

Further useful cocatalyst components are borane or carborane compounds such as
7,8-dicarbaundecaborane(13),
undecahydrido-7,8-dimethyl-7,8-dicarbaundecaborane,
dodecahydrido-1-phenyl-1,3-dicarbanonaborane,
tri(butyl)ammonium undecahydrido-8-ethyl-7,9-dicarbaundecaborate,
4-carbanonaborane(14),
bis(tri(butyl)ammonium) nonaborate,
bis(tri(butyl)ammonium) undecaborate,
bis(tri(butyl)ammonium) dodecaborate,
bis(tri(butyl)ammonium) decachlorodecaborate,
tri(butyl)ammonium 1-carbadecaborate,
tri(butyl)ammonium 1-carbadodecaborate,
tri(butyl)ammonium 1-trimethylsilyl-1-carbadecaborate,
tri(butyl)ammonium bis(nonahydrido-1,3-dicarbanonaborato)cobaltate(III),
tri(butyl)ammonium bis(undecahydrido-7,8-dicarbaundecaborato)ferrate(III).

Combinations of at least one of the abovementioned amines and a support with organoelement compounds as described in WO 99/40129 are likewise of importance as cocatalyst systems.

Preferred constituents of these cocatalyst systems are the compounds of the formulae (A) and (B),

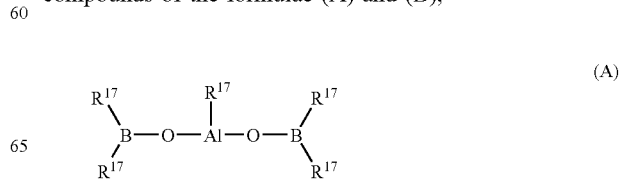

(A)

-continued

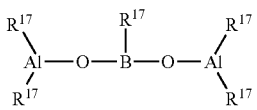
(B)

where
R$^{17}$ is a hydrogen atom, a halogen atom, a C$_1$–C$_{40}$ group, in particular C$_1$–C$_{20}$-alkyl, C$_1$–C$_{20}$-haloalkyl, C$_1$–C$_{10}$-alkoxy, C$_6$–C$_{20}$-aryl, C$_6$–C$_{20}$-haloaryl, C$_6$–C$_{20}$-aryloxy, C$_7$–C$_{40}$-arylalkyl, C$_7$–C$_{40}$-haloarylalkyl, C$_7$–C$_{40}$-alkylaryl or C$_7$–C$_{40}$-haloalkylaryl.

R$^{17}$ can also be an —OSiR$^{18}_3$ group, where R$^{18}$ are identical or different and are as defined for R$^{17}$.

Further preferred cocatalysts are compounds in general which are formed by reaction of at least one compound of the formula (C) and/or (D) and/or (E) with at least one compound of the formula (F):

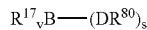
(C)

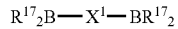
(D)

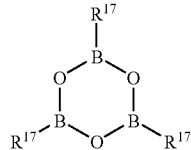
(E)

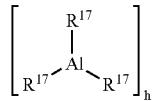
(F)

where
R$^{80}$ can be a hydrogen atom or a boron-free C$_1$–C$_{40}$ group such as C$_1$–C$_{20}$-alkyl, C$_6$–C$_{20}$-aryl, C$_7$–C$_{40}$-arylalkyl, C$_7$–C$_{40}$-alkylaryl and
R$^{17}$ is as defined above,
X$^1$ is an element of main group VI of the Periodic Table of the Elements or an NR group, where R is a hydrogen atom or a C$_1$–C$_{20}$-hydrocarbon radical such as C$_1$–C$_{20}$-alkyl or C$_1$–C$_{20}$-aryl,
D is an element of main group VI of the Periodic Table of the Elements or an NR group, where R is a hydrogen atom or a C$_1$–C$_{20}$-hydrocarbon radical such as C$_1$–C$_{20}$-alkyl or C$_1$–C$_{20}$-aryl,
v is an integer from 0 to 3,
s is an integer from 0 to 3,
h is an integer from 1 to 10,
B is boron,
Al is aluminum.

If desired, the organoelement compounds may be combined with an organometallic compound of the formulae III to V and/or VII [M$^{40}$R$^{19}_b$]$_d$, where M$^{40}$ is an element of main group I, II or III of the Periodic Table of the Elements, R$^{19}$ are identical or different and are each a hydrogen atom, a halogen atom, a C$_1$–C$_{40}$ group, in particular a C$_1$–C$_{20}$-alkyl, C$_6$–C$_{40}$-aryl, C$_7$–C$_{40}$-arylalkyl or C$_7$–C$_{40}$-alkylaryl group, b is an integer from 1 to 3 and d is an integer from 1 to 4.

Examples of cocatalytically active compounds of the formulae A and B are

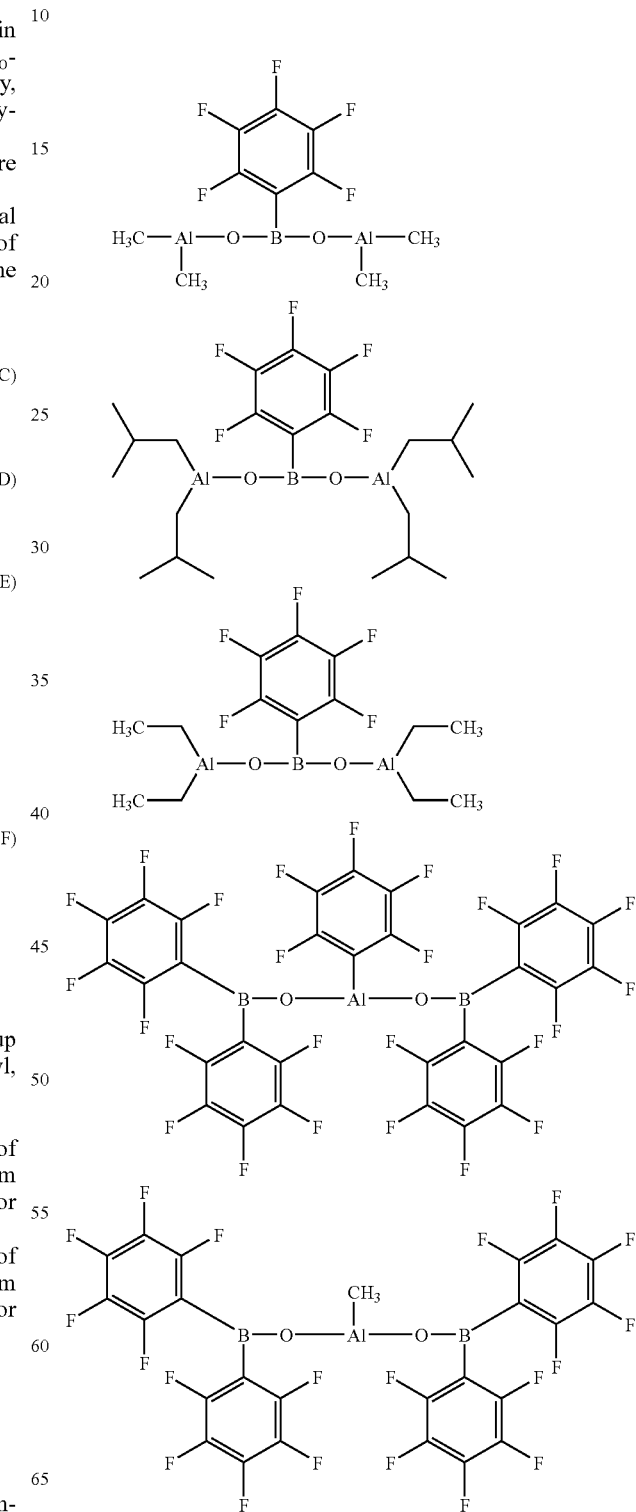

-continued

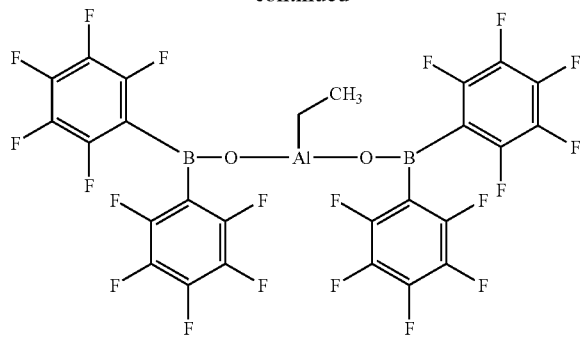

The organometallic compounds of the formula VII are preferably uncharged Lewis acids in which $M^{40}$ is lithium, magnesium and/or aluminum, in particular aluminum. Examples of preferred organometallic compounds of the formula XII are trimethylaluminum, triethylaluminum, triisopropylaluminum, trihexylaluminum, trioctylaluminum, tri-n-butylaluminum, tri-n-propylaluminum, triisoprenylaluminum, dimethylaluminum monochloride, diethylaluminum monochloride, diisobutylaluminum monochloride, methylaluminum sesquichloride, ethylaluminum sesquichloride, dimethylaluminum hydride, diethylaluminum hydride, diisopropylaluminum hydride, dimethylaluminum trimethylsiloxide, dimethylaluminum triethylsiloxide, phenylalane, pentafluorophenylalane and o-tolylalane.

Further cocatalysts, which may be in an unsupported or supported form, are the compounds described in EP-A-924223, DE-A-19622207, EP-A-601830, EP-A-824112, EP-A-824113, EP-A-811627, WO97/11775 and DE-A-19606167.

The support components of the catalyst system of the invention can be any inert, organic or inorganic solid, in particular a porous support such as talc, inorganic oxides and finely divided polymer powders (e.g. polyolefins).

Suitable inorganic oxides may be found among oxides of elements of main group II-VI of the Periodic Table and transition groups III-IV of the Periodic Table of the Elements. Examples of oxides preferred as supports include silicon dioxide, aluminum oxide and also mixed oxides of the elements calcium, aluminum, silicon, magnesium, titanium and corresponding oxide mixtures, and also hydrotalcites. Other inorganic oxides which can be used alone or in combination with the abovementioned preferred oxidic supports are, for example, MgO, $ZrO_2$, $TiO_2$ or $B_2O_3$, to name only a few.

The support materials used have a specific surface area in the range from 10 to 1000 $m^2/g$, a pore volume in the range from 0.1 to 5 ml/g and a mean particle size of from 1 to 500 μm. Preference is given to supports having a specific surface area in the range from 50 to 500 μm, a pore volume in the range from 0.5 to 3.5 ml/g and a mean particle size in the range from 5 to 350 μm. Particular preference is given to supports having a specific surface area in the range from 200 to 400 $m^2/g$, a pore volume in the range from 0.8 to 3.0 ml/g and a mean particle size of from 10 to 200 μm.

If the support material used naturally has a low moisture content or residual solvent content, dehydration or drying before use can be dispensed with. If this is not the case, as when using silica gel as support material, dehydration or drying is advisable. Thermal dehydration or drying of the support material can be carried out under reduced pressure with simultaneous blanketing with inert gas (e.g. nitrogen). The drying temperature is in the range from 100 to 1000° C., preferably from 200 to 800° C. The parameter pressure is not critical in this case. The duration of the drying process can be from 1 to 24 hours. Shorter or longer drying times are possible provided that equilibrium with the hydroxyl groups on the support surface can be established under the conditions selected, which normally takes from 4 to 8 hours.

It is also possible to dehydrate or dry the support material by chemical means, by reacting the adsorbed water and the hydroxyl groups on the surface with suitable passivating agents. The reaction with the passivating reagent can convert all or some of the hydroxyl groups into a form which leads to no adverse interactions with the catalytically active centers. Suitable passivating agents are, for example, silicon halides and silanes, e.g. silicon tetrachloride, chlorotrimethylsilane, dimethylaminotrichlorosilane, or organometallic compounds of aluminum, boron and magnesium, for example trimethylaluminum, triethylaluminum, triisobutylaluminum, triethylborane, dibutylmagnesium. Chemical dehydration or passivation of the support material is carried out by, for example, reacting a suspension of the support material in a suitable solvent with the passivating reagent in pure form or as a solution in a suitable solvent in the absence of air and moisture. Suitable solvents are, for example, aliphatic or aromatic hydrocarbons such as pentane, hexane, heptane, toluene or xylene. Passivation is carried out at temperatures of from 25° C. to 120° C., preferably from 50 to 70° C. Higher and lower temperatures are possible. The reaction time is from 30 minutes to 20 hours, preferably from 1 to 5 hours. After the chemical dehydration is complete, the support material is isolated by filtration under inert conditions, washed one or more times with suitable inert solvents as described above and subsequently dried in a stream of inert gas or under reduced pressure. Organic support materials such as finely divided polyolefin powders (e.g. polyethylene, polypropylene or polystyrene) can also be used and should likewise be freed of adhering moisture, solvent residues or other impurities by means of appropriate purification and drying operations before use.

To prepare the supported catalyst system, at least one of the above-described transition metal compounds of the formula I is brought into contact with at least one cocatalyst component in a suitable solvent, preferably giving a soluble reaction product, an adduct or a mixture.

The preparation obtained in this way is then mixed with the dehydrated or passivated support material, the solvent is removed and the resulting supported transition metal catalyst system is dried to ensure that all or most of the solvent is removed from the pores of the support material. The supported catalyst is obtained as a free-flowing powder.

One process for preparing a free-flowing and, if desired, prepolymerized transition metal catalyst system comprises the following steps:

a) preparation of a transition metal compound/cocatalyst mixture in a suitable solvent or suspension medium, with the transition metal component having one of the above-described structures,
b) application of the transition metal compound/cocatalyst mixture to a porous, preferably inorganic, dehydrated support,
c) removal of the major part of the solvent from the resulting mixture,
d) isolation of the supported catalyst system,
e) if desired, prepolymerization of the resulting supported catalyst system using one or more olefinic monomer(s) to obtain a prepolymerized supported catalyst system.

Preferred solvents for the preparation of the transition metal compound/cocatalyst mixture are hydrocarbons and hydrocarbon mixtures which are liquid at the reaction temperature selected and in which the individual compounds preferably dissolve. However, solubility of the individual components is not a prerequisite as long as it is ensured that the reaction product of transition metal compound and cocatalyst component is soluble in the solvent selected. Examples of suitable solvents include alkanes such as pentane, isopentane, hexane, heptane, octane and nonane; cycloalkanes such as cyclopentane and cyclohexane; and aromatics such as benzene, toluene, ethylbenzene and diethylbenzene. Very particular preferably is given to toluene.

The amounts of aluminoxane and transition metal compound used in the preparation of the supported catalyst system can be varied within a wide range. Preference is given to a molar ratio of aluminum to transition metal in the transition metal compounds of from 10:1 to 1000:1, very particularly preferably from 50:1 to 500:1. In the case of methylaluminoxane, preference is given to using 30% strength toluene solutions; however, the use of 10% solutions is also possible.

To preactivate the transition metal compound, the solid compound is dissolved in a solution of the aluminoxane in a suitable solvent. However, it is also possible to dissolve the transition metal compound separately in a suitable solvent and subsequently to combine this solution with the aluminoxane solution. Preference is given to using toluene.

The preactivation time is from 1 minute to 200 hours.

The preactivation can take place at room temperature (25° C.). The use of higher temperatures can in particular cases shorten the preactivation time required and give an additional increase in activity. In this case, the term higher temperature refers to a range from 50 to 100° C.

The preactivated solution or the transition metal compound/cocatalyst mixture is subsequently combined with an inert support material, usually silica gel, in the form of a dry powder or as a suspension in one of the abovementioned solvents. The support material is preferably used as powder. The order of addition is immaterial. The preactivated transition metal compound/cocatalyst solution or the transition metal compound/cocatalyst mixture can be added to the initially charged support material, or else the support material can be introduced into the initially charged solution.

The volume of the preactivated solution or of the transition metal compound/cocatalyst mixture can exceed 100% of the total pore volume of the support material used or can be up to 100% of the total pore volume.

The temperature at which the preactivated solution or the transition metal compound/cocatalyst mixture is brought into contact with the support material can vary in the range from 0 to 100° C. However, lower or higher temperatures are also possible.

All or most of the solvent is subsequently removed from the supported catalyst system, with the mixture being able to be stirred and, if desired, also heated.

Preference is given to removing both the visible proportion of the solvent and also the proportion present in the pores of the support material. Removal of the solvent can be carried out in a conventional way under reduced pressure and/or by flushing with inert gas. During drying, the mixture can be heated until the free solvent has been removed, which usually takes from 1 to 3 hours at a preferably selected temperature of from 30 to 60° C. The free solvent is the visible proportion of solvent in the mixture. For the purposes of the present invention, residual solvent is the proportion enclosed in the pores.

As an alternative to complete removal of the solvent, the supported catalyst system can also be dried only to a particular residual solvent content, with the free solvent having been completely removed. The supported catalyst system can subsequently be washed with a low-boiling hydrocarbon such as pentane or hexane and dried again.

The supported catalyst system prepared according to the invention can either be used directly for the polymerization of olefins or can be prepolymerized using one or more olefinic monomers prior to being used in a polymerization process. The procedure for carrying out prepolymerization of supported catalyst systems is described, for example, in WO 94/28034.

As additive, a small amount of an olefin, preferably an α-olefin (for example vinylcyclohexane, styrene or phenyldimethylvinylsilane), as modifying component or an antistatic (as described in U.S. Ser. No. 08/365,280) can be added during or after the preparation of the supported catalyst system. The molar ratio of additive to nonmetallocene component compound I is preferably from 1:1000 to 1000:1, very particularly preferably from 1:20 to 20:1.

The present invention also provides a process for preparing a polyolefin by polymerization of one or more olefins in the presence of the catalyst system of the invention comprising at least one transition metal component of the formula VII. For the purposes of the present invention, the term polymerization encompasses both homopolymerization and copolymerization.

Preference is given to polymerizing olefins of the formula $R_m$—CH=CH—$R_n$, where $R_m$ and $R_n$ are identical or different and are each a hydrogen atom or an organic radical having from 1 to 20 carbon atoms, in particular from 1 to 10 carbon atoms, and $R_m$ and $R_n$ together with the atoms connecting them may form one or more rings. Examples of such olefins are 1-olefins having 2–20, preferably from 2 to 10, carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. In the process of the invention, preference is given to homopolymerizing ethene or propene or copolymerizing propene with ethene and/or with one or more 1-olefins having from 4 to 20 carbon atoms, e.g. butene, hexene, styrene or vinylcyclohexane, and/or one or more dienes having from 4 to 20 carbon atoms, e.g. 1,4-butadiene, norbornadiene, ethylidenenorbornene or ethylnorbornadiene. Examples of such copolymers are ethene-propene copolymers, ethane-norbornene, ethane-styrene or ethane-propene-1,4-hexadiene terpolymers. The polymerization is carried out at a temperature of from 0 to 300° C., preferably from 50 to 200° C., very particularly preferably 50–80° C. The pressure is from 0.5 to 2000 bar, preferably from 5 to 64 bar.

The polymerization can be carried out in solution, in bulk, in suspension or in the gas phase, continuously or batchwise, in one or more stages.

The catalyst system prepared according to the invention can be used as sole catalyst component for the polymerization of olefins having from 2 to 20 carbon atoms, but is preferably used in combination with at least one alkyl compound of the elements of main groups I to III of the Periodic Table, e.g. an aluminum alkyl, magnesium alkyl or lithium alkyl or an aluminoxane. The alkyl compound is added to the monomer or suspension medium and serves to free the monomer of substances which can impair the activity of the catalyst. The amount of alkyl compound added depends on the quality of the monomers used.

As molar mass regulator and/or to increase the activity, hydrogen is added if necessary.

The catalyst system can be introduced into the polymerization system in pure form or can be admixed with inert components such as paraffins, oils or waxes to improve meterability. In addition, an antistatic can be introduced into the polymerization system either together with or separately from the catalyst system used.

The polymers prepared by means of the catalyst system of the invention display a uniform particle morphology and contain no fines. No deposits or cake material occur in the polymerization using the catalyst system of the invention.

The invention will be illustrated by the following examples which do not, however, restrict the scope of the invention.

General procedures: Preparation and handling of the organometallic compounds were carried out in the absence of air and moisture under argon (Schlenk technique or glove box). All solvents required were purged with argon and dried over molecular sieves before use.

1. Preparation of the Ligands

Example 1 trans-N,N'-bispyridin-2-ylmethylenecyclohexane-1,2-diamine

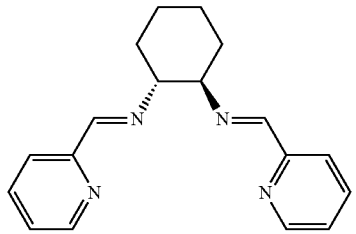

15.0 g (0.13 mol) of trans-1,2-diaminocyclohexane are dissolved in 80 ml of methanol and, at room temperature, 28.1 g (0.26 mol) of pyridine-2-aldehyde are added a little at a time. The solution is refluxed for one hour and then cooled to room temperature. The precipitated solid is filtered off and dried in an oil pump vacuum. The product is obtained in the form of a light-yellow powder in a yield of 23 g (79 mmol, 60%). $^1$H-NMR (400 MHz, CDCl$_3$): δ=8.55 (m, 2H, Py), 8.31 (s, 2H, =C—H), 7.88, 7.63, 7.21 (3×m, 6H, Py), 3.52 (m, 2H, NC—H), 1.90–1.49 (m, 8H, (CH$_2$)$_4$) ppm.

Example 2 trans-N,N'-bispyridin-2-ylcyclohexane-1,2-diamine

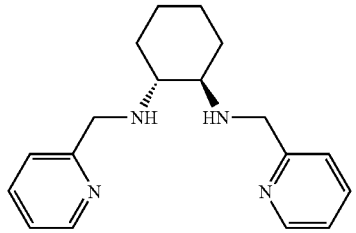

5 g (17 mmol) of trans-N,N'-bispyridin-2-ylmethylenecyclo-hexane-1,2-diamine together with 41 ml of methanol are placed in a reaction vessel and, at room temperature, 1.35 g (35.7 mmol) of sodium borohydride are added a little at a time while stirring. After the addition is complete, the reaction mixture is refluxed for one hour. After cooling to room temperature, 30 ml of water are added and the product is extracted with 3×100 ml of dichloromethane. The combined organic phases are dried over magnesium sulfate and the solvent is removed under reduced pressure, giving the product in the form of a light-yellow oil in a yield of 5 g (16.9 mmol, 99%) and a purity of 96% (according to GC). $^1$H-NMR (400 MHz, CDCl$_3$): δ=8.52, 7.62, 7.39, 7.14 (4×m, 8H, Py), 4.03 (d, J=14 Hz, 2H benzyl. CH$_2$), 3.84 (d, J=14 Hz, 2H benzyl. CH$_2$), 2.50 (s, br, 2H, NH), 2.32 (m, 2H, NCH), 2.16–1.07 (m, 8H, (CH$_2$)$_4$) ppm.

Example 3

N'-[2'-(Dimethylaminomethyleneamino)-[1,1']binaphthalenyl-2-yl]-N,N-dimethylformamidine

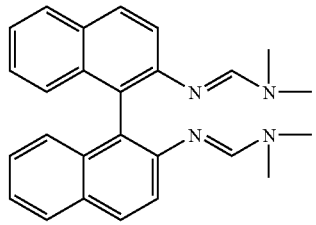

9.3 g (52.5 mmol) of 2-pyridinesulfonyl chloride are stirred in 175 ml of N,N-dimethylformamide for 5 minutes at room temperature. 10 g (35 mmol) of 2,2'-diamino-1,1'-binaphthyl are then added and mixture is stirred at room temperature for another 5 minutes. The solvent is removed under reduced pressure and the brown residue is admixed with 100 ml of a 4M potassium carbonate solution and 200 ml of tert-butyl methyl ether. The aqueous phase is extracted with 3×100 ml of tert-butyl methyl ether, the combined organic phases, are dried over magnesium sulfate and the solvent is removed under reduced pressure. The crude product obtained in this way is recrystallized from methanol, giving the desired product in the form of light-yellow crystals in a yield of 10.3 g (74%, 26 mmol). $^1$H-NMR (400 MHz, CDCl$_3$): δ=7.71–7.39 (m, 14 H, aromat. H, N═CH), 2.83 (s, 12H, CH$_3$) ppm.

Example 4

N$^2$,N$^2$-Bisdimethylaminomethyl-[1,1']binaphthalenyl-2,2'-diamine

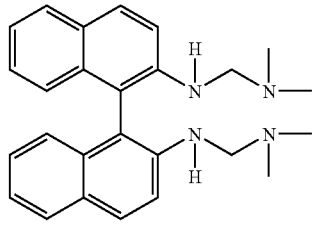

0.96 g (25.3 mmol) of sodium borohydride is added a little at a time at room temperature to 5 g (12.6 mmol) of N'-[2'-(dimethylaminomethyleneamino)-[1,1']binaphthalenyl-2-yl]-N,N-dimethylformamidine in 80 ml of methanol. After the addition is complete, the reaction mixture is refluxed for one hour. After cooling to room temperature, 60 ml of water are added and the product is extracted with 3×100 ml of dichloromethane. The combined organic phases are dried over magnesium sulfate and the solvent is removed under reduced pressure, giving the product in the form of a light-yellow oil in a yield of 4.9 g (12.3 mmol, 98%) and a purity of 97% (according to GC). $^1$H-NMR (400 MHz, CDCl$_3$): δ=7.55–6.82 (m, 12H, aromat. H), 4.13 (s, 4H, NHCH$_2$NMe$_2$), 2.75 (s, br, 2H, NH), 2.27 (s, 12H, NMe$_2$) ppm.

Example 5 trans-N,N'-Bis(2-diphenylphosphanylbenzylidene)cyclohexane-1,2-diamine

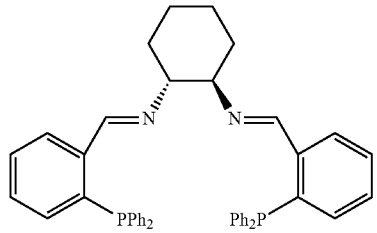

7.5 g of granulated molecular sieves (4A) are baked in a Schlenk tube. After addition of 50 ml of dichloromethane, 1.75 g (15 mmol) of trans-1,2-diaminocyclohexane and 8.7 g (30 mmol) of o-diphenylphosphinobenzaldehyde, the reaction mixture is stirred for 24 hours. After filtration through Celite, the solvent is removed and the residue is recrystallized with 50 ml of ethanol, giving the product in the form of a light-yellow powder in a yield of 8.6 g (13 mmol, 87%). $^1$H-NMR (400 MHz, CDCl$_3$): δ=8.71 (d, J=4 Hz, 2H, N═C—H), 7.78–6.64 (m, 28 H, aromat. H), 3.16 (m, 2H, C—H), 1.66–1.31 (m, 8H, (CH$_2$)$_4$) ppm.

Example 6 trans-N,N'-Bis(2-diphenylphosphanylbenzyl)cyclohexane-1,2-diamine

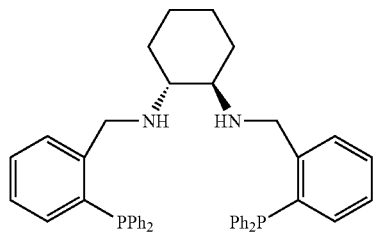

1.14 g (30 mmol) of sodium borohydride are added a little at a time to a solution of 3.30 g (5.0 mmol) of trans-N,N'-bis(2-diphenylphosphanylbenzylidene)cyclohexane-1,2-diamine in 60 ml of methanol. The solution is refluxed for 24 hours and, after cooling to room temperature, admixed with 20 ml of water. The organic phase is extracted with 3×50 ml of dichloromethane and the combined organic phases are washed with 2×30 ml of 10% ammonium chloride solution and 30 ml of water. After drying over magnesium sulfate, the solvent is removed under reduced pressure and the residue is recrystallized from 30 ml of ethanol. The product precipitates in the form of light-yellow crystals in a yield of 2.68 g (4.0 mmol, 80%). $^1$H-NMR (400 MHz, CDCl$_3$): δ=7.65–6.92 (m, 28 H, aromat. H), 4.11, 3.98 (2×d, J=13.4 Hz, 4 H, Ar—CH$_2$), 2.21 (m, 2H, NCH), 1.63–1.27 (m, 8H, (CH$_2$)$_4$) ppm.

2. Preparation of Complexes

General procedures: All reactions were carried out under a protective Ar atmosphere. Some of the complexes prepared are paramagnetic and can therefore not be characterized by NMR spectroscopy.

Example 7

(trans-N,N'-Bispyridin-2-ylmethylenecyclohexane-1,2-diamine)-iron(II) chloride

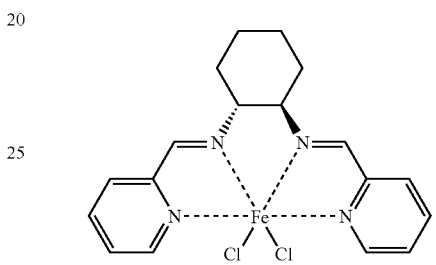

In a baked Schlenk tube, 1.0 g (3.4 mmol) of trans-N,N'-bispyridin-2-ylmethylenecyclohexane-1,2-diamine are dissolved in 40 ml of THF and admixed with 431 mg (3.4 mmol) of iron(II) chloride (anhydrous). After 0.5 h, the solution becomes dark blue. After stirring at room temperature for another 2 hours, the solvent is removed under reduced pressure and the residue is stirred with 10 ml of heptane. Filtration through a G3 frit gives the product as a dark blue solid in a yield of 1.41 g (3.36 mmol, 99%).

Example 8

(trans-N,N'-Bispyridin-2-ylmethylenecyclohexane-1,2-diamine)-nickel(II) bromide

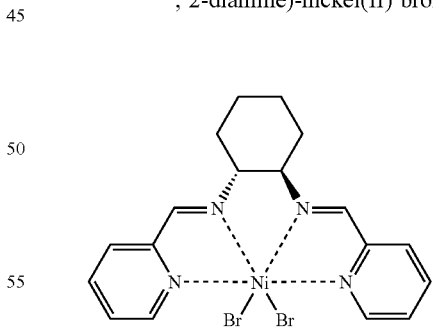

In a baked Schlenk tube, 1.0 g (3.4 mmol) of trans-N,N'-bispyridin-2-ylmethylenecyclohexane-1,2-diamine are dissolved in 40 ml of THF and admixed with 1.04 g (3.4 mmol) of nickel(II) bromide*DME. After 0.2 h, the solution becomes dark. After stirring at room temperature for another 2 hours, the solvent is removed under reduced pressure and the residue is stirred with 10 ml of heptane. Filtration through a G3 frit gives the product as a dark blue solid in a yield of 1.32 g (2.58 mmol, 76%).

Example 9

(trans-N,N'-Bispyridin-2-ylmethylenecyclohexane-1,2-diamine)-palladium(II) chloride

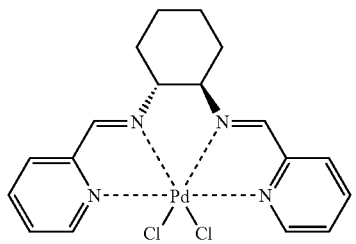

In a baked Schlenk tube, 1.0 g (3.4 mmol) of trans-N,N'-bispyridin-2-ylmethylenecyclohexane-1,2-diamine are dissolved in 40 ml of THF and admixed with 882 mg (3.4 mmol) of palladium(II) chloride*2 CH₃CN. After 0.2 h, the solution becomes yellowish. After stirring at room temperature for another 2 hours, the solvent is removed under reduced pressure and the residue is stirred with 10 ml of heptane. Filtration through a G3 frit gives the product as a yellow solid in a yield of 1.45 g (2.92 mmol, 86%).

Example 10

(N'-[2'-(Dimethylaminomethyleneamino)-[1,1']binaphthalenyl-2-yl]-N,N-dimethylformamidine)iron(II) chloride

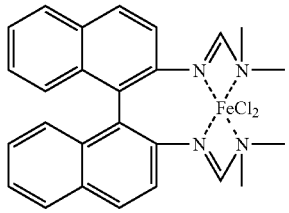

In a baked Schlenk tube, 1.0 g (2.5 mmol) of N'-[2'-(dimethylaminomethyleneamino)-[1,1']binaphthalenyl-2-yl]-N,N-dimethylformamidine is dissolved in 40 ml of THF and admixed with 317 mg (2.5 mmol) of iron(II) chloride (anhydrous). After 0.5 h, the solution becomes dark blue. After stirring at room temperature for a further 2 hours, the solvent is removed under reduced pressure and the residue is stirred with 10 ml of heptane. Filtration through a G3 frit gives the product as a dark blue solid in a yield of 1.01 g (1.9 mmol, 78%).

Example 11

(N'-[2'-(Dimethylaminomethyleneamino)-[1,1']binaphthalenyl-2-yl]-N,N-dimethylformamidine)nickel(II) bromide

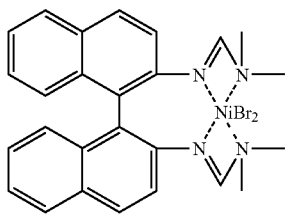

In a baked Schlenk tube, 1.0 g (2.5 mmol) of N'-[2'-(dimethylaminomethyleneamino)-[1,1']binaphthalenyl-2-yl]-N,N-dimethylformamidine is dissolved in 40 ml of THF and admixed with 772 mg (2.5 mmol) of nickel(II) bromide*DME. After 0.2 h, the solution becomes dark. After stirring at room temperature for a further 2 hours, the solvent is removed under reduced pressure and the residue is stirred with 10 ml of heptane. Filtration through a G3 frit gives the product as a dark blue solid in a yield of 1.17 g (1.9 mmol, 76%).

Example 12

(N'-[2'-(Dimethylaminomethyleneamino)-[1,1']binaphthalenyl-2-yl]-N,N-dimethylformamidine)palladium(II) chloride

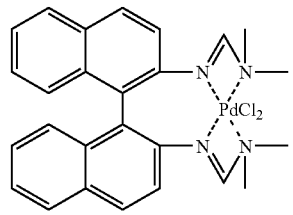

In a baked Schlenk tube, 1.0 g (2.5 mmol) of N'-[2'-(dimethylaminoethyleneamino)-[1,1']binaphthalenyl-2-yl]-N,N-dimethylformamidine is dissolved in 40 ml of THF and admixed with 649 mg (2.5 mmol) of palladium(II) chloride * 2 CH₃CN. After 0.2 h, the solution becomes yellowish. After stirring at room temperature for a further 2 hours, the solvent is removed under reduced pressure and the residue is stirred with 10 ml of heptane. Filtration through a G3 frit gives the product as a yellow solid in a yield of 1.45 g (2.48 mmol, 99%).

Example 13

(trans-N,N'-Bis(2-diphenylphosphanylbenzylidene)cyclohexane-1,2-diamine)iron(II) chloride

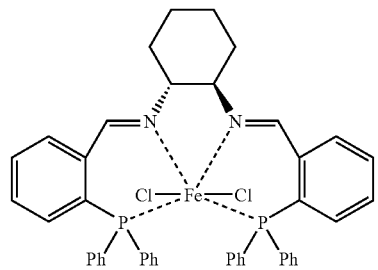

In a baked Schlenk tube, 1.0 g (1.5 mmol) of trans-N,N'-bis(2-diphenylphosphanylbenzylidene)cyclohexane-1,2-diamine is dissolved in 40 ml of THF and admixed with 190 mg (1.5 mmol) of iron(II) chloride (anhydrous). After 0.5 h, the solution becomes dark blue. After stirring at room temperature for a further 2 hours, the solvent is removed under reduced pressure and the residue is stirred with 10 ml of heptane. Filtration through a G3 frit gives the product as a dark blue solid in a yield of 0.98 g (1.2 mmol, 83%).

Example 14

(trans-N,N'-Bis(2-diphenylphosphanylbenzylidene)cyclohexane-1,2-diamine)nickel(II) bromide

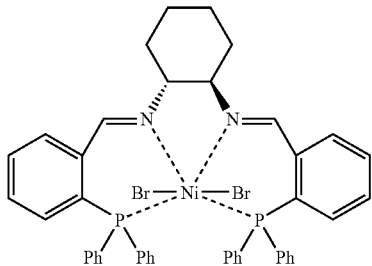

In a baked Schlenk tube, 1.0 g (1.5 mmol) of trans-N,N'-bis(2-diphenylphosphanylbenzylidene)cyclohexane-1,2-diamine is dissolved in 40 ml of THF and admixed with 463 mg (1.5 mmol) of nickel(II) bromide*DME. After 0.2 h, the solution becomes dark. After stirring at room temperature for a further 2 hours, the solvent is removed under reduced pressure and the residue is stirred with 10 ml of heptane. Filtration through a G3 frit gives the product as a dark blue solid in a yield of 1.22 g (1.4 mmol, 93%).

Example 15

(trans-N,N'-Bis(2-diphenylphosphanylbenzylidene)cyclohexane-1,2-diamine)palladium(II) chloride

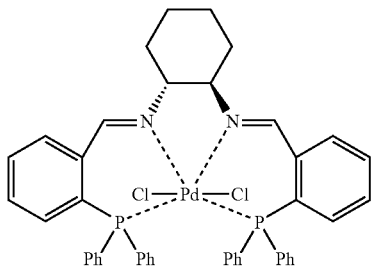

In a baked Schlenk tube, 1.0 g (1.5 mmol) of trans-N,N'-bis(2-diphenylphosphanylbenzylidene)cyclohexane-1,2-diamine is dissolved in 40 ml of THF and admixed with 389 mg (1.5 mmol) of palladium(II) chloride*2 CH$_3$CN. After 0.2 h, the solution becomes yellowish. After stirring at room temperature for a further 2 hours, the solvent is removed under reduced pressure and the residue is stirred with 10 ml of heptane. Filtration through a G3 frit gives the product as a yellow solid in a yield of 1.03 g (1.2 mmol, 82%).

Example 16

(trans-N,N'-Bispyridin-2-ylmethylenecyclohexane-1,2-diamido)-dibenzylzirconium

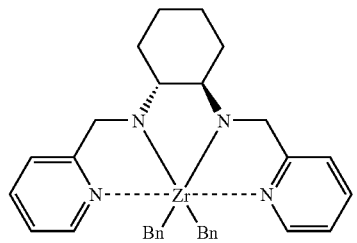

1.0 g (3.4 mmol) of trans-N,N'-bispyridin-2-ylcyclohexane-1,2-diamine together with 20 ml of toluene/THF 10:1 are placed in a baked Schlenk tube and admixed at −30° C. with a solution of 1.5 g (3.4 mmol) of tetrabenzylzirconium in 10 ml of toluene. After the addition is complete, the mixture is stirred at −30° C. for another 1 hour and stirred overnight at room temperature. The solvent is evaporated to a volume of 7 ml and the solution is stored overnight at −30° C. The precipitate obtained in this way is isolated by filtration through a G4 frit and dried in an oil pump vacuum. The product is obtained in the form of a powder in a yield of 0.89 g (1.57 mmol, 46%). $^1$H-NMR (CDCl$_3$, 400 MHz): δ=8.61–6.92 (m, 18H, Py, aromat. H), 4.72, 4.03 (2×m, J, 2H benzyl. NCH$_2$), 3.88 (m, 2H, NCH), 2.26–1.13 (m, 12H, ZrCH$_2$, (CH$_2$)$_4$) ppm.

Example 17

(N$^2$,N$^{2'}$-Bisdimethylaminomethyl-[1,1']binaphthalenyl-2,2'-diamido)-dibenzylzirconium

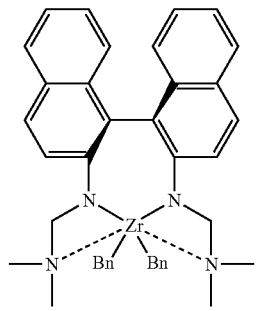

1.0 g (2.5 mmol) of N$^2$,N$^{2'}$-bisdimethylaminomethyl-[1,1']binaphthalenyl-2,2'-diamine in 20 ml of toluene/THF 10:1 is placed in a baked Schlenk tube and admixed at −30° C. with a solution of 1.14 g (2.5 mmol) of tetrabenzylzirconium in 10 ml of toluene. After the addition is complete, the mixture is stirred at −30° C. for another 1 hour and stirred overnight at room temperature. The solvent is evaporated to a volume of 11 ml and the solution is stored overnight at −30° C. The precipitate obtained in this way is isolated by filtration through a G4 frit and dried in an oil pump vacuum. The product is obtained in the form of a powder in a yield of 1.01 g (1.5 mmol, 60%). $^1$H-NMR (CDCl$_3$, 400 MHz): δ=7.95–6.81 (m, 22H, aromat. H), 4.32 (m, 4H, NCH$_2$), 2.73 (s, 12H, CH$_3$), 1.25 (s, 4H, ZrCH$_2$) ppm.

Example 18

(trans-N,N'-Bis(2-diphenylphosphanylbenzyl)cyclohexane-1,2-diamido)dichlorozirconium

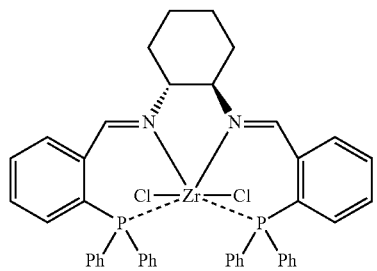

2.0 g (3.0 mmol) of trans-N,N'-bis(2-diphenylphosphanylbenzyl)cyclohexane-1,2-diamine in 20 ml of diethylether are placed in a baked Schlenk tube and admixed at 0° C. with 2.4 ml of n-butyllithium (6 mmol, 2.5 M in toluene). The mixture is stirred overnight at room temperature and 704 mg (3.0 mmol) of zirconium tetrachloride are then added. After stirring at room temperature for five hours, the solvent is removed under reduced pressure. The residue is stirred with 20 ml of dichloromethane and filtered through Celite. The solvent is removed and the crude product obtained in this way is recrystallized from 10 ml of toluene/heptane 7:3. Filtration through a G4 frit gives the product in the form of a grey powder in a yield of 1.87 g. $^1$H-NMR (CDCl$_3$, 400 MHz): δ=8.11–6.89 (m, 28 H, aromat. H), 3.69 (s, 4H, NCH$_2$), 3.11 (m, 2H, NCH), 1.43–0.99 (m, 8H, (CH$_2$)$_4$) ppm.

What is claimed is:

1. A catalyst system comprising at least one cocatalyst in combination with a supported compound of the formula I

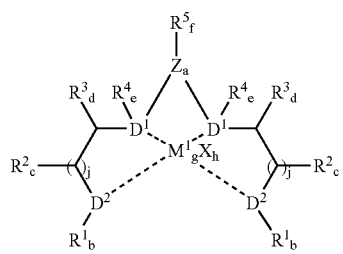

formula I where

M$^1$ is a metal of groups III to XII of the Periodic Table of the Elements and

D$^1$ are identical or different and are each a donor atom of group XV or XVI of the Periodic Table of the Elements and D$^2$ are identical or different and are each a donor atom of group XV of XVI of the Periodic Table of The Elements and Z is a bridging structural element between the two donor atoms D$^1$ and X are identical or different and are each a hydrogen atom, a C$_1$–C$_{10}$-hydrocarbon group or a halogen atom or OR$^6$, SR$^6$, OSO$_2$R$^6$, OSi(R$^6$)$_3$, Si(R$^6$)$_3$, P(R$^6$)$_2$, P(R$^6$)$_3$, NCR$^6$, N(R$^6$)$_3$, B(R$^6$)$_4$, substituted or unsubstituted pyridine or N(R$^6$)$_2$, and R$^1$ are identical or different and are each a hydrogen atom, a C$_1$–C$_{20}$-alkyl group, a C$_6$–C$_{20}$-aryl group, a C$_7$–C$_{20}$-alkylaryl group, a C$_7$–C$_{30}$-arylalkyl group, a C$_2$–C$_{20}$-alkenyl group, a C$_2$–C$_{20}$-alkynyl group or a halogen-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or a heteroatom-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or Si(R$^6$)$_3$, where one or more radicals R$^1$ together with one or more radicals R$^2$ may form a monocyclic or polycyclic ring system, which may in turn be substituted by one or more radicals R$^6$, and R$^2$ are identical or different and are each a hydrogen atom, a C$_1$–C$_{20}$-alkyl group, a C$_6$–C$_{20}$-aryl group, a C$_7$–C$_{20}$-alkylaryl group, a C$_7$–C$_{30}$-arylalkyl group, a C$_2$–C$_{20}$-alkenyl group, a C$_2$–C$_{20}$-alkynyl group or a halogen-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or a heteroatom-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or Si(R$^6$)$_3$, where one or more radicals R$^2$ together with one or more radicals R$^1$ and/or R$^3$ may form a monocyclic or polycyclic ring system, which may in turn be substituted by one or more radicals R$^6$, and R$^3$ are identical or different and are each a hydrogen atom, a C$_1$–C$_{20}$-alkyl group, a C$_6$–C$_{20}$-aryl group, a C$_7$–C$_{20}$-alkylaryl group, a C$_7$–C$_{30}$-arylalkyl group, a C$_2$–C$_{20}$-alkenyl group, a C$_2$–C$_{20}$ alkynyl group or a halogen-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or a heteroatom-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or Si(R$^6$)$_3$, where one or more radicals R$^3$ together with one or more radicals R$^2$ may form a monocyclic or polycyclic ring system; which may in turn be substituted by one or more radicals R$^6$, and R$^4$ are identical or different and are each a hydrogen atom, a C$_1$–C$_{20}$-alkyl group, a C$_6$–C$_{20}$-aryl group, a C$_7$–C$_{20}$-alkylaryl group, a C$_7$–C$_{30}$-arylalkyl group, a C$_2$–C$_{20}$-alkenyl group, a C$_2$–C$_{20}$-alkynyl group or a halogen-containing C$_1$–C$_{20}$-alkyl group, C$_6$–C$_{20}$-aryl group, C$_7$–C$_{20}$-alkylaryl group, C$_1$–C$_{30}$-arylalkyl group, C$_2$–C$_{20}$-alkenyl group, C$_2$–C$_{20}$-alkynyl group or a heteroatom-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group or C$_2$–C$_{20}$-alkynyl group, and R$^5$ are identical or different and are each a hydrogen atom, a C$_1$–C$_{20}$-alkyl group, a C$_6$–C$_{20}$-aryl group, a C$_7$–C$_{20}$-alkylaryl group, a C$_7$–C$_{30}$-arylalkyl group, a C$_2$–C$_{20}$-alkenyl group, a C$_2$–C$_{20}$-alkynyl group or a halogen-containing C$_1$–C$_{20}$-alkyl group, C$_6$–C$_{20}$-aryl group, C$_7$–C$_{20}$-alkylaryl group, C$_7$–C$_{30}$-arylalkyl group, C$_2$–C$_{20}$-alkenyl group, C$_2$–C$_{20}$-alkynyl group or a heteroatom-containing C$_1$–C$_{20}$-alkyl group, C$_6$–C$_{20}$-aryl group, C$_7$–C$_{20}$-alkylaryl group, C$_7$–C$_{30}$-arylalkyl group, $C_2$–$C_{20}$-alkenyl group, $C_2$–$C_{20}$-alkynyl group, where a plurality of radicals $R^5$ may together form a monocyclic or polycyclic ring system, and $R^6$ are identical or different and are each a hydrogen atom, a halogen atom, a $C_1$–$C_{10}$-alkyl group, a $C_6$–$C_{20}$-aryl group, a $C_7$–$C_{20}$-alkylaryl group, a $C_7$–$C_{30}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or a heteroatom-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group, and a are identical or different and are each an integer from 1 to 10 and b are identical or different and are each an integer from 0 to 3 and c are identical or different and are each an integer from 0 to 2 and d are identical or different and are each an integer from 0 to 2 and e are identical or different and are each an integer from 0 to 2 and f are identical or different and are each an integer from 2 to 20 and g are identical or different and are each 1 or 2 and h are identical or different and are each an integer from 1 to 4 and i are identical or different and are each an integer from 0 to 24 and j are identical or different and are each an integer from 0 to 10, with the proviso that complexes in which $Z_a(R^5)_f$ is unsubstituted or substituted ethyl and $D^1$ is nitrogen, $R^3$ is hydrogen, d is 1 and two $R^2$ together form a substituted benzene ring which is substituted by $D^2$=O are excluded.

2. A catalyst system as claimed in claim 1, wherein $M^1$ is selected from the group consisting of Sc, Y, La, Ti, Zr, Hf, V, Cr, Mo, Mn, Fe, Ru, Co, Rh, Ni, Pd, and Cu and $D^1$ are identical or different and are each selected from the group consisting of N, P, As, O, S, Se, and Te and $D^2$ are identical or different and are each selected from the group consisting of N, P, As, O, S, Se, and Te.

3. A catalyst system as claimed in claim 1, wherein $D^1$-$Z^1(R^5)_f$-$D^1$ is a structure selected from the group consisting of IIa to IIz formula II a-z II a
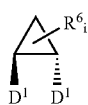

II b
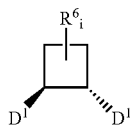

II c
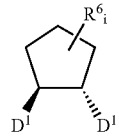

II d
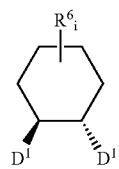

II e
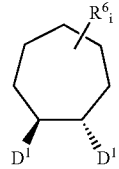

II f
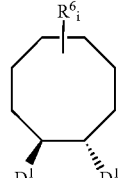

II g
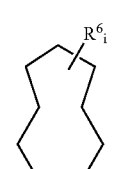

II h
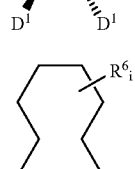

II i
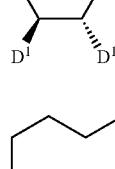

II j
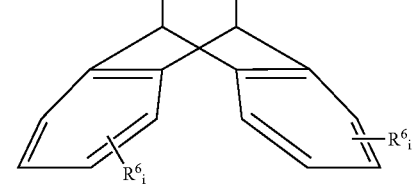

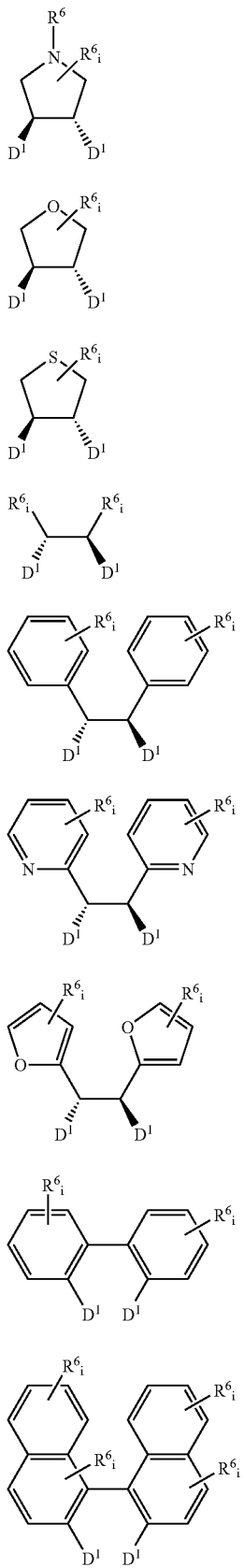

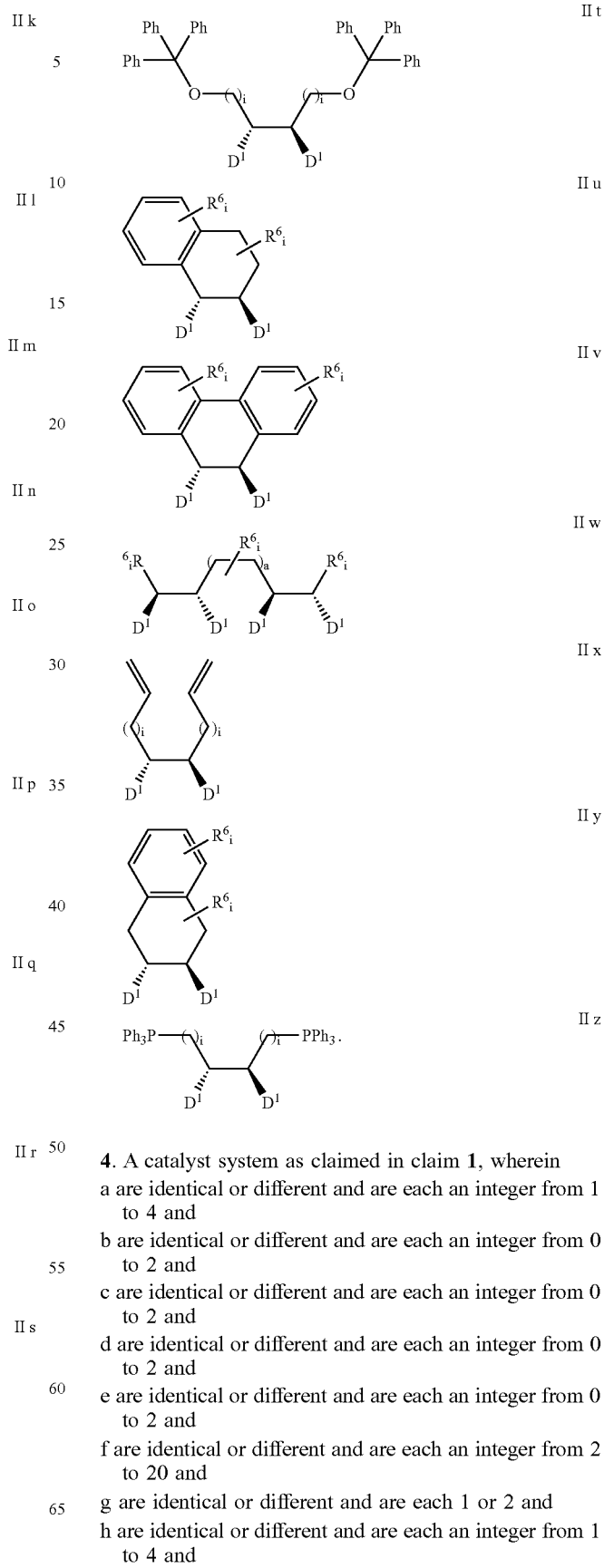

4. A catalyst system as claimed in claim 1, wherein
a are identical or different and are each an integer from 1 to 4 and
b are identical or different and are each an integer from 0 to 2 and
c are identical or different and are each an integer from 0 to 2 and
d are identical or different and are each an integer from 0 to 2 and
e are identical or different and are each an integer from 0 to 2 and
f are identical or different and are each an integer from 2 to 20 and
g are identical or different and are each 1 or 2 and
h are identical or different and are each an integer from 1 to 4 and i are identical or different and are each an integer from 0 to 24 and j are identical or different and are each an integer from 0 to 10.

5. A catalyst system as claimed in claim 3, wherein $M^1$ is selected from the group consisting of Ti, Zr, Hf, Fe, Co, Ni, and Pd and $D^1$ are identical or different and are each selected from the group consisting of N, P, O, and S, and $D^2$ are identical or different and are each selected from the group consisting of N, P, O, and S, and Z corresponds to one of the formulae II d, II j, II o, II r or II s and X are identical or different and are each selected from the group consisting of chloride, bromide, iodide, methyl, ethyl, propyl, ethenyl, propynyl, phenyl, benzyl, methoxy, trifluoromethanesulfonyl, dimethylamido, tetrafluoroborate, triphenylphosphine, acetonitrile, trimethylsilyl, and pyridine, and $R^1$ are identical or different and are each a selected from the group consisting of hydrogen, methyl, ethyl, propyl, i-propyl, tert-butyl, phenyl, benzyl, trimethylsilyl, and tert-butyldimethylsilyl, or a radical $R^1$ together with a radical $R^2$ forms a monocyclic or polycyclic ring system, which may in turn be substituted by one or more radicals $R^6$, and $R^2$ are identical or different and are each selected from the group consisting of hydrogen, methyl, ethyl, propyl, i-propyl, tert-butyl, phenyl, benzyl, trimethylsilyl, and tert-butyldimethylsilyl, or a radical $R^2$ together with a radical $R^1$ forms a monocyclic or polycyclic ring system, which may in turn be substituted by one or more radicals $R^6$, and $R^3$ are identical or different and are each selected from the group consisting of hydrogen, methyl, ethyl, propyl, i-propyl, tert-butyl, phenyl, benzyl, trimethylsilyl, and tert-butyldimethylsilyl, and $R^4$ are identical or different and are each a selected from the group consisting of hydrogen, methyl, ethyl, propyl, i-propyl, tert-butyl, phenyl, benzyl, trimethylsilyl, and tert-butyldimethylsilyl, and R5 identical or different and are each a selected from the group consisting of hydrogen, methyl, ethyl, propyl, i-propyl, tert-butyl, phenyl, benzyl, trimethylsilyl, and tert-butyldimethylsilyl, or a plurality of radicals $R^5$ may together form a monocyclic or polycyclic ring system, and $R^6$ are identical or different and are each a selected from the group consisting of hydrogen, fluorine, chlorine, bromine, iodine, methyl, ethyl, propyl, i-propyl, tert-butyl, phenyl, benzyl, trimethylsilyl, and tert-butyldimethylsilyl, and a are identical or different and are each 1 or 2 and b are identical or different and are each an integer from 0 to 2 and c are identical or different and are each an integer from 0 to 2 and d are identical or different and are each an integer from 0 to 2 and e are identical or different and are each 0 or 1 and f are identical or different and are each an integer from 2 to 20 and g are identical or different and are each 1 or 2 and h are identical or different and are each an integer from 1 to 4 and i are identical or different and are each an integer from 0 to 18 and j are identical or different and are each an integer from 0 to 6.

6. A catalyst system as claimed in claim 1, wherein $M^1$ is selected from the group consisting of Sc, Y, La, Ti, Zr, Hf, V, Cr, Mo, Mn, Fe, Ru, Co, Rh, Ni, Pd, and Cu.

7. A catalyst system as claimed in claim 1, wherein $D^1$ is a donor atom of the group consisting of N, P, As, O, S, Se, and Te.

8. A catalyst system as claimed in claim 1, wherein $D^2$ is a donor atom of the group consisting of N, P, As, O, S, Se, and Te.

9. A catalyst system as claimed in claim 1, wherein X is a $C_1$–$C_{10}$ hydrocarbon selected from the group consisting of $C_1$–$C_{10}$-alkyl, $C_6$–$C_{10}$-aryl, $C_7$–$C_{20}$-alkylaryl, $C_7$–$C_{20}$-arylalkyl, $C_2$–$C_{20}$-alkenyl, and $C_2$–$C_{20}$-alkynyl.

* * * * *